（12）United States Patent
Wisnewski et al.

(10) Patent No.: US 7,666,641 B2
(45) Date of Patent: Feb. 23, 2010

(54) CANINE COX-2 PROTEINS AND USES THEREOF

(75) Inventors: Nancy Wisnewski, Fort Collins, CO (US); Kevin S. Brandt, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 0 days.

(21) Appl. No.: 12/352,511

(22) Filed: Jan. 12, 2009

(65) Prior Publication Data

US 2009/0123957 A1 May 14, 2009

Related U.S. Application Data

(62) Division of application No. 11/372,770, filed on Mar. 10, 2006, now Pat. No. 7,476,524, which is a division of application No. 10/679,140, filed on Oct. 2, 2003, now Pat. No. 7,223,578, which is a division of application No. 09/919,060, filed on Jul. 31, 2001, now Pat. No. 6,638,744.

(60) Provisional application No. 60/224,486, filed on Aug. 11, 2000.

(51) Int. Cl.
*C12N 9/02* (2006.01)
*C12P 21/04* (2006.01)
*C12N 1/20* (2006.01)
*C12N 15/00* (2006.01)
*C12Q 1/68* (2006.01)
*C07H 21/02* (2006.01)
*C07H 21/04* (2006.01)
*C12Q 1/00* (2006.01)
*C12Q 1/26* (2006.01)

(52) U.S. Cl. .................. 435/189; 435/4; 435/6; 435/25; 435/69.1; 435/71.1; 435/252.3; 435/320.1; 435/440; 536/23.1; 536/23.2

(58) Field of Classification Search .......... None
See application file for complete search history.

(56) References Cited

U.S. PATENT DOCUMENTS 6,638,744 B2 10/2003 Wisnewski et al.
7,223,578 B2 5/2007 Wisnewski et al.

OTHER PUBLICATIONS

Dubois et al., 1998, *The FASEB Journal*, vol. 12, pp. 1063-1072.
Giuliano et al., 1999, *British Journal of Pharmacology*, vol. 126, pp. 1824-1830.
Golden et al., 1999, *Rheumatic Disease Clinics of North America*, vol. 25, No. 2, pp. 359-378.
Khan et al., 1998, *Toxicologic Pathology*, vol. 26, No. 5, pp. 612-620.
Laufer et al., 1999, *Inflamm. res.*, vol. 48, pp. 133-138.
Masferrer et al., 1994, *Proc. Natl. Acad. Sci. USA*, vol. 91, pp. 3228-3232.
Ricketts et al., 1998, *AJVR*, vol. 59, No. 11, pp. 1441-1446.
Riendeau et al., 1997, *Can. J. Physiol. Pharmacol.*, vol. 75, pp. 1088-1095.
Seibert et al., 1994, *Proc. Natl. Acad. Sci. USA*, vol. 91, pp. 12013-12017.
Vane et al., 1998, *Annu. Rev. Pharmacol. Toxicol.*, vol. 38, pp. 97-120.
Vane et al., 1995, *Inflamm Res*, vol. 44, pp. 1-10.
Warner et al., 1999, *Proc. Natl. Acad. Sci. USA*, vol. 96, pp. 7563-7568.

*Primary Examiner*—Yong D Pak
(74) *Attorney, Agent, or Firm*—Sheridan Ross P.C.

(57) ABSTRACT

The present invention relates to canine COX-1 and COX-2 proteins; to canine COX-1 and COX-2 nucleic acid molecules, including those that encode such COX-1 and COX-2 proteins, respectively; to antibodies raised against such proteins; and to compounds that inhibit the activity of such proteins. The present invention also includes methods to obtain such proteins, nucleic acid molecules, antibodies, and inhibitory compounds. The present invention also includes therapeutic compositions comprising such inhibitory compounds, particularly those that specifically inhibit COX-2 activity, as well as the use of such therapeutic compositions to treat animals.

15 Claims, No Drawings

SEQUENCE LISTING

```
<160> NUMBER OF SEQ ID NOS: 25

<210> SEQ ID NO 1
<211> LENGTH: 542
<212> TYPE: DNA
<213> ORGANISM: Canis familiaris
<220> FEATURE:
<221> NAME/KEY: CDS
<222> LOCATION: (2)..(541)
<223> OTHER INFORMATION:

<400> SEQUENCE: 1 ccc cgg tca cat ttg att gag agt cca cca act tat aat gtg aac tac       49
    Pro Arg Ser His Leu Ile Glu Ser Pro Pro Thr Tyr Asn Val Asn Tyr
    1               5                  10                  15 ggc tat aaa agc tgg gaa gcc ttt tct aac ctc tcc tat tat acc aga       97
Gly Tyr Lys Ser Trp Glu Ala Phe Ser Asn Leu Ser Tyr Tyr Thr Arg
                20                  25                  30 gct ctt ccc cct gta cct gat gac tgt cca aca ccc atg ggt gtg aaa     145
Ala Leu Pro Pro Val Pro Asp Asp Cys Pro Thr Pro Met Gly Val Lys
            35                  40                  45 ggc aag aaa gag ctt cct gat tca aaa gag att gtg gaa aag ttt ctt     193
Gly Lys Lys Glu Leu Pro Asp Ser Lys Glu Ile Val Glu Lys Phe Leu
        50                  55                  60 ctg cga aga aag ttc att cct gat ccc caa ggc acc aat atg atg ttt     241
Leu Arg Arg Lys Phe Ile Pro Asp Pro Gln Gly Thr Asn Met Met Phe
65                  70                  75                  80 gca ttc ttt gcc cag cac ttt acc cat caa ttt ttc aag aca gat cat     289
Ala Phe Phe Ala Gln His Phe Thr His Gln Phe Phe Lys Thr Asp His
                85                  90                  95 aag cga gga cca gct ttc acc aaa gga ttg ggc cat ggg gtg gac tta     337
Lys Arg Gly Pro Ala Phe Thr Lys Gly Leu Gly His Gly Val Asp Leu
            100                 105                 110 aat cat gtt tat ggg gaa act ttg gat aga caa cat aaa ctg cgc ctt     385
Asn His Val Tyr Gly Glu Thr Leu Asp Arg Gln His Lys Leu Arg Leu
        115                 120                 125 ttc aag gat gga aaa atg aaa tat cag gta att gat gga gag gtg tat     433
Phe Lys Asp Gly Lys Met Lys Tyr Gln Val Ile Asp Gly Glu Val Tyr
    130                 135                 140 cct cct acc gtc aaa gat act cag gtc gag atg atc tac cca cct cat     481
Pro Pro Thr Val Lys Asp Thr Gln Val Glu Met Ile Tyr Pro Pro His
145                 150                 155                 160 gtt cct gaa cac ctg cag ttt gct gtg ggc caa gag gtc ttt ggt cct     529
Val Pro Glu His Leu Gln Phe Ala Val Gly Gln Glu Val Phe Gly Pro
                165                 170                 175 ggt gcc ctg gtc t                                                    542
Gly Ala Leu Val
```

-continued

<210> SEQ ID NO 2
<211> LENGTH: 180
<212> TYPE: PRT
<213> ORGANISM: Canis familiaris

<400> SEQUENCE: 2

Pro Arg Ser His Leu Ile Glu Ser Pro Thr Tyr Asn Val Asn Tyr
1               5                   10                  15

Gly Tyr Lys Ser Trp Glu Ala Phe Ser Asn Leu Ser Tyr Tyr Thr Arg
            20                  25                  30

Ala Leu Pro Pro Val Pro Asp Asp Cys Pro Thr Pro Met Gly Val Lys
        35                  40                  45

Gly Lys Lys Glu Leu Pro Asp Ser Lys Glu Ile Val Glu Lys Phe Leu
    50                  55                  60

Leu Arg Arg Lys Phe Ile Pro Asp Pro Gln Gly Thr Asn Met Met Phe
65                  70                  75                  80

Ala Phe Phe Ala Gln His Phe Thr His Gln Phe Phe Lys Thr Asp His
                85                  90                  95

Lys Arg Gly Pro Ala Phe Thr Lys Gly Leu Gly His Gly Val Asp Leu
            100                 105                 110

Asn His Val Tyr Gly Glu Thr Leu Asp Arg Gln His Lys Leu Arg Leu
        115                 120                 125

Phe Lys Asp Gly Lys Met Lys Tyr Gln Val Ile Asp Gly Glu Val Tyr
    130                 135                 140

Pro Pro Thr Val Lys Asp Thr Gln Val Glu Met Ile Tyr Pro Pro His
145                 150                 155                 160

Val Pro Glu His Leu Gln Phe Ala Val Gly Gln Glu Val Phe Gly Pro
                165                 170                 175

Gly Ala Leu Val
            180

<210> SEQ ID NO 3
<211> LENGTH: 542
<212> TYPE: DNA
<213> ORGANISM: Canis familiaris

<400> SEQUENCE: 3
agaccagggc accaggacca aagacctctt ggcccacagc aaactgcagg tgttcaggaa      60
catgaggtgg gtagatcatc tcgacctgag tatctttgac ggtaggagga tacacctctc     120
catcaattac ctgatatttc attttttccat ccttgaaaag gcgcagttta tgttgtctat    180
ccaaagtttc cccataaaca tgatttaagt ccaccccatg gcccaatcct ttggtgaaag     240
ctggtcctcg cttatgatct gtcttgaaaa attgatgggt aaagtgctgg caaagaatg      300
caaacatcat attggtgcct ggggatcag gaatgaactt cttcgcaga agaaactttt       360
ccacaatctc tttgaatca ggaagctctt tcttgccttt cacacccatg ggtgttggac      420
agtcatcagg tacaggggga agagctctgg tataatagga gaggttagaa aaggcttccc     480
agctttata gccgtagttc acattataag ttggtggact ctcaatcaaa tgtgaccggg      540
ga                                                                   542

<210> SEQ ID NO 4
<211> LENGTH: 3509
<212> TYPE: DNA
<213> ORGANISM: Canis familiaris
<220> FEATURE:
<221> NAME/KEY: CDS
<222> LOCATION: (53)..(1864)
<223> OTHER INFORMATION:

<400> SEQUENCE: 4

| | | | | | |
|---|---|---|---|---|---|
| ccgccgcctc tgccaccgcc cgcgctccgc ccgcgccccg cccgccgccg cg atg ctg | | | | | 58 |
| | | | | Met Leu | |
| | | | | 1 | |

| gcc cgc gcc ctg gtg ctc tgc gcc gcc ctg gcg gtc gtc cgc gca gca | 106 |
|---|---|
| Ala Arg Ala Leu Val Leu Cys Ala Ala Leu Ala Val Val Arg Ala Ala | |
| 5 10 15 | |

| aat cct tgc tgt tcc cac cca tgt caa aac caa ggt att tgt atg agc | 154 |
|---|---|
| Asn Pro Cys Cys Ser His Pro Cys Gln Asn Gln Gly Ile Cys Met Ser | |
| 20 25 30 | |

| aca gga ttt gac cag tat aag tgt gac tgt acc cga aca gga ttc tac | 202 |
|---|---|
| Thr Gly Phe Asp Gln Tyr Lys Cys Asp Cys Thr Arg Thr Gly Phe Tyr | |
| 35 40 45 50 | |

| ggc gaa aac tgc tca aca ccg gaa ttt ctg aca aga ata aaa tta tac | 250 |
|---|---|
| Gly Glu Asn Cys Ser Thr Pro Glu Phe Leu Thr Arg Ile Lys Leu Tyr | |
| 55 60 65 | |

| ctg aaa ccc act cca aat aca gta cac tac ata ctt acc cac ttc aag | 298 |
|---|---|
| Leu Lys Pro Thr Pro Asn Thr Val His Tyr Ile Leu Thr His Phe Lys | |
| 70 75 80 | |

| gga gtc tgg aac att gtc aat aac atc ccc ttc ctg cga aat aca att | 346 |
|---|---|
| Gly Val Trp Asn Ile Val Asn Asn Ile Pro Phe Leu Arg Asn Thr Ile | |
| 85 90 95 | |

| atg aaa tat gtg ttg aca tcc cgg tca cat ttg att gag agt cca cca | 394 |
|---|---|
| Met Lys Tyr Val Leu Thr Ser Arg Ser His Leu Ile Glu Ser Pro Pro | |
| 100 105 110 | |

| act tat aat gtg aac tac ggc tat aaa agc tgg gaa gcc ttt tct aac | 442 |
|---|---|
| Thr Tyr Asn Val Asn Tyr Gly Tyr Lys Ser Trp Glu Ala Phe Ser Asn | |
| 115 120 125 130 | |

| ctc tcc tat tat acc aga gct ctt ccc cct gta cct gat gac tgt cca | 490 |
|---|---|
| Leu Ser Tyr Tyr Thr Arg Ala Leu Pro Pro Val Pro Asp Asp Cys Pro | |
| 135 140 145 | |

| aca ccc atg ggt gtg aaa ggc aag aaa gag ctt cct gat tca aaa gag | 538 |
|---|---|
| Thr Pro Met Gly Val Lys Gly Lys Lys Glu Leu Pro Asp Ser Lys Glu | |
| 150 155 160 | |

| att gtg gaa aag ttt ctt ctg cga aga aag ttc att cct gat ccc caa | 586 |
|---|---|
| Ile Val Glu Lys Phe Leu Leu Arg Arg Lys Phe Ile Pro Asp Pro Gln | |
| 165 170 175 | |

| ggc acc aat atg atg ttt gca ttc ttt gcc cag cac ttt acc cat caa | 634 |
|---|---|
| Gly Thr Asn Met Met Phe Ala Phe Phe Ala Gln His Phe Thr His Gln | |
| 180 185 190 | |

| ttt ttc aag aca gat cat aag cga gga cca gct ttc acc aaa gga ttg | 682 |
|---|---|
| Phe Phe Lys Thr Asp His Lys Arg Gly Pro Ala Phe Thr Lys Gly Leu | |
| 195 200 205 210 | |

| ggc cat ggg gtg gac tta aat cat gtt tat ggg gaa act ttg gat aga | 730 |
|---|---|
| Gly His Gly Val Asp Leu Asn His Val Tyr Gly Glu Thr Leu Asp Arg | |
| 215 220 225 | |

| caa cat aaa ctg cgc ctt ttc aag gat gga aaa atg aaa tat cag gta | 778 |
|---|---|
| Gln His Lys Leu Arg Leu Phe Lys Asp Gly Lys Met Lys Tyr Gln Val | |
| 230 235 240 | |

| att gat gga gag gtg tat cct cct acc gtc aaa gat act cag gtc gag | 826 |
|---|---|
| Ile Asp Gly Glu Val Tyr Pro Pro Thr Val Lys Asp Thr Gln Val Glu | |
| 245 250 255 | |

| atg atc tac cca cct cat gtt cct gaa cac ctg cag ttt gct gtg ggc | 874 |
|---|---|
| Met Ile Tyr Pro Pro His Val Pro Glu His Leu Gln Phe Ala Val Gly | |
| 260 265 270 | |

```
cag gag gtc ttt ggt ctg gtg cct ggt ctg atg atg tat gcc acc att      922
Gln Glu Val Phe Gly Leu Val Pro Gly Leu Met Met Tyr Ala Thr Ile
275                 280                 285                 290 tgg ctg cgg gag cat aac aga gtg tgt gat gtg ctt aaa cag gag cac      970
Trp Leu Arg Glu His Asn Arg Val Cys Asp Val Leu Lys Gln Glu His
                    295                 300                 305 cca gaa tgg gat gat gag cgg tta ttc cag acg agc agg cta ata ctt     1018
Pro Glu Trp Asp Asp Glu Arg Leu Phe Gln Thr Ser Arg Leu Ile Leu
            310                 315                 320 ata gga gaa acc att aag att gtg att gaa gac tat gta caa cac ttg     1066
Ile Gly Glu Thr Ile Lys Ile Val Ile Glu Asp Tyr Val Gln His Leu
325                 330                 335 agt ggc tat cac ttc aag ctg aag ttt gac cca gag ctg ctt ttc aac     1114
Ser Gly Tyr His Phe Lys Leu Lys Phe Asp Pro Glu Leu Leu Phe Asn
    340                 345                 350 caa caa ttc cag tac caa aac cgc att gct gct gag ttt aac aca ctc     1162
Gln Gln Phe Gln Tyr Gln Asn Arg Ile Ala Ala Glu Phe Asn Thr Leu
355                 360                 365                 370 tac cac tgg cat ccc ctc ctg cct gac acc ttg caa ata gat gac cag     1210
Tyr His Trp His Pro Leu Leu Pro Asp Thr Leu Gln Ile Asp Asp Gln
                375                 380                 385 gag tac aat ttc caa cag ttt atc tac aac aac tct ata tta ttg gaa     1258
Glu Tyr Asn Phe Gln Gln Phe Ile Tyr Asn Asn Ser Ile Leu Leu Glu
            390                 395                 400 cat ggc ctt acc cag ttt gtg gaa tca ttc agc agg caa att gct ggc     1306
His Gly Leu Thr Gln Phe Val Glu Ser Phe Ser Arg Gln Ile Ala Gly
405                 410                 415 agg gtt gcc ggt ggc agg aat gtt cca gct gca gta caa caa gta gca     1354
Arg Val Ala Gly Gly Arg Asn Val Pro Ala Ala Val Gln Gln Val Ala
    420                 425                 430 aaa gct tcg att gac cag agc aga cag atg aaa tac cag tct ctt aat     1402
Lys Ala Ser Ile Asp Gln Ser Arg Gln Met Lys Tyr Gln Ser Leu Asn
435                 440                 445                 450 gag tat cgc aaa cgc ttt agg ctg aag ccc tat aca tca ttc gaa gaa     1450
Glu Tyr Arg Lys Arg Phe Arg Leu Lys Pro Tyr Thr Ser Phe Glu Glu
                455                 460                 465 ctt aca gga gag aag gaa atg gct gcg ggg ttg gag gcc ctt tat ggt     1498
Leu Thr Gly Glu Lys Glu Met Ala Ala Gly Leu Glu Ala Leu Tyr Gly
            470                 475                 480 gat att gat gcc atg gag ctg tat cct gcc ctc ttg gta gaa aag cct     1546
Asp Ile Asp Ala Met Glu Leu Tyr Pro Ala Leu Leu Val Glu Lys Pro
        485                 490                 495 cgt cca gat gcc atc ttt ggt gag acc atg gta gaa atg gga gca cca     1594
Arg Pro Asp Ala Ile Phe Gly Glu Thr Met Val Glu Met Gly Ala Pro
500                 505                 510 ttc tcc ttg aaa gga ctt atg ggt aat ccc atc tgt tca cct gac tac     1642
Phe Ser Leu Lys Gly Leu Met Gly Asn Pro Ile Cys Ser Pro Asp Tyr
515                 520                 525                 530 tgg aag cct agc acc ttt ggt gga gaa gta ggc ttt aaa atc atc aac     1690
Trp Lys Pro Ser Thr Phe Gly Gly Glu Val Gly Phe Lys Ile Ile Asn
                535                 540                 545 act gcc tca atc cag tct ctc atc tgc aat aac gtg aag ggc tgt cca     1738
Thr Ala Ser Ile Gln Ser Leu Ile Cys Asn Asn Val Lys Gly Cys Pro
            550                 555                 560 ttc act gca ttc tct gtt caa gac gga caa ctc acc aaa aca gtc acc     1786
Phe Thr Ala Phe Ser Val Gln Asp Gly Gln Leu Thr Lys Thr Val Thr
        565                 570                 575 att aat gca agc tct tcg cac tcc ggt cta gat gac atc aat ccc aca     1834
Ile Asn Ala Ser Ser Ser His Ser Gly Leu Asp Asp Ile Asn Pro Thr
580                 585                 590
```

```
gtc cta ctg aaa gaa cgg tca act gaa cta tagaagcctg ttaatcctat    1884
Val Leu Leu Lys Glu Arg Ser Thr Glu Leu
595                 600 ttatttattt atatggacga ttccttttaa cttaattatt taatatttat gttaaactcc    1944
ttatgttact taacatctgt taaggagaaa ggggtcatac ttgtgaagat tttcatgtca    2004
ctattttaaa gatgtcttcg ggttaaagag gaaaacagtt ttctgtttta taaatgagtt    2064
tgacatcctt ttacttgaat tcagtttat attattatta tgaacaaaag cgaagatgtt    2124
ggatatttaa atgctgttcc aggatgacaa aatgctgcaa gttttttttcg acactatcgg    2184
gatttctagt gtatcttccc tggtgcatta gaagcaacta cctgcacact ttcttttctt    2244
ctgttagcca ctgtgctggt agaaactctc ttctgatcag tttactttct tgtttccttg    2304
attttttaaga tctgagtata cctttctttg gactctgtct atactttctt acctgaactt    2364
gtgtaagttt tcaggaaaac ctcaactcag gactactagt aatttagctc ctcttaagag    2424
gaatgaaagg aaaaaaaaaa cagcccttaa aggactctat acacaacagt atacacttat    2484
tttaagtgaa aggcagcgat cttttttgtaa attaattta aattgtaaca gaaggcttca    2544
atgaggctaa tgactgacaa agaactgtag ggggttcttg atggaaggaa gtcgtatttc    2604
tattaagaat atcctttctc atttaaaagc aaagtcaaat tctgaatagt tcccgggaag    2664
ataatgtttc ttttccacat ctcattgtca gctgacattt gctggtactg tatacttaat    2724
ttattgagga ttattatttg ttttgttagg atgttattat aaactaggtt taagctgcaa    2784
tcatttttttt tttttttgca ttatgtgaga atcagtatat cttctttgag attaactctg    2844
aattattatg taaacactaa gagaaattat ttgagatctg tgagtaaatt ttcaggaacc    2904
caactctggt atattgaaat atggcaagtt ggaattgaaa tatagatttc cctatatacc    2964
agcccacaga gaacactgtg tctcattaac ctgcatgtac cataagatct ttacagtttt    3024
gagggacyta tgratccttc attaagtcat tcagctataa cttattgagg acacaggtgc    3084
aaatatcact tgtgggtttt aatattttt gtggattctt aatattttta aatcatgcac    3144
ttgattacag ataacatcag tatttgtaaa tgagaaagca tgtctttagg tagagaaaga    3204
aaatgaaatt ttattaaagg aaataactca ggggaatttt taagatttta tgtttaaaaa    3264
gttaagaaat agtcaatatt agaagggctt atgtaaaaac cttttttaact tcactgaaag    3324
aaattttgtt attaatatca aagccgactg aattcggagt ataatatatg aatgttttgg    3384
tgcctcagac aaatgtgtat ttaaattaac ttatgtaaga tgtaagtgtt aacaaatgcc    3444
tgtttatttt tatactatct aagaatgaaa aatctcttct aaaataaatt tttgactgtt    3504
tccat    3509
```

```
<210> SEQ ID NO 5
<211> LENGTH: 604
<212> TYPE: PRT
<213> ORGANISM: Canis familiaris

<400> SEQUENCE: 5

Met Leu Ala Arg Ala Leu Val Leu Cys Ala Ala Leu Ala Val Val Arg
1               5                   10                  15

Ala Ala Asn Pro Cys Cys Ser His Pro Cys Gln Asn Gln Gly Ile Cys
            20                  25                  30

Met Ser Thr Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
```

-continued

```
            50                  55                  60
Leu Tyr Leu Lys Pro Thr Pro Asn Thr Val His Tyr Ile Leu Thr His
 65                  70                  75                  80

Phe Lys Gly Val Trp Asn Ile Val Asn Asn Ile Pro Phe Leu Arg Asn
                 85                  90                  95

Thr Ile Met Lys Tyr Val Leu Thr Ser Arg Ser His Leu Ile Glu Ser
            100                 105                 110

Pro Pro Thr Tyr Asn Val Asn Tyr Gly Tyr Lys Ser Trp Glu Ala Phe
            115                 120                 125

Ser Asn Leu Ser Tyr Tyr Thr Arg Ala Leu Pro Pro Val Pro Asp Asp
130                 135                 140

Cys Pro Thr Pro Met Gly Val Lys Gly Lys Lys Glu Leu Pro Asp Ser
145                 150                 155                 160

Lys Glu Ile Val Glu Lys Phe Leu Leu Arg Arg Lys Phe Ile Pro Asp
            165                 170                 175

Pro Gln Gly Thr Asn Met Met Phe Ala Phe Phe Ala Gln His Phe Thr
            180                 185                 190

His Gln Phe Phe Lys Thr Asp His Lys Arg Gly Pro Ala Phe Thr Lys
            195                 200                 205

Gly Leu Gly His Gly Val Asp Leu Asn His Val Tyr Gly Glu Thr Leu
            210                 215                 220

Asp Arg Gln His Lys Leu Arg Leu Phe Lys Asp Gly Lys Met Lys Tyr
225                 230                 235                 240

Gln Val Ile Asp Gly Glu Val Tyr Pro Pro Thr Val Lys Asp Thr Gln
            245                 250                 255

Val Glu Met Ile Tyr Pro Pro His Val Pro Glu His Leu Gln Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
            290                 295                 300

Glu His Pro Glu Trp Asp Asp Glu Arg Leu Phe Gln Thr Ser Arg Leu
305                 310                 315                 320

Ile Leu Ile Gly Glu Thr Ile Lys Ile Val Ile Glu Asp Tyr Val Gln
            325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ala Glu Phe Asn
            355                 360                 365

Thr Leu Tyr His Trp His Pro Leu Leu Pro Asp Thr Leu Gln Ile Asp
370                 375                 380

Asp Gln Glu Tyr Asn Phe Gln Phe Ile Tyr Asn Asn Ser Ile Leu
385                 390                 395                 400

Leu Glu His Gly Leu Thr Gln Phe Val Glu Ser Phe Ser Arg Gln Ile
            405                 410                 415

Ala Gly Arg Val Ala Gly Gly Arg Asn Val Pro Ala Ala Val Gln Gln
            420                 425                 430

Val Ala Lys Ala Ser Ile Asp Gln Ser Arg Gln Met Lys Tyr Gln Ser
            435                 440                 445

Leu Asn Glu Tyr Arg Lys Arg Phe Arg Leu Lys Pro Tyr Thr Ser Phe
            450                 455                 460

Glu Glu Leu Thr Gly Glu Lys Glu Met Ala Ala Gly Leu Glu Ala Leu
465                 470                 475                 480
```

Tyr Gly Asp Ile Asp Ala Met Glu Leu Tyr Pro Ala Leu Leu Val Glu
           485                 490                 495

Lys Pro Arg Pro Asp Ala Ile Phe Gly Glu Thr Met Val Glu Met Gly
           500                 505                 510

Ala Pro Phe Ser Leu Lys Gly Leu Met Gly Asn Pro Ile Cys Ser Pro
           515                 520                 525

Asp Tyr Trp Lys Pro Ser Thr Phe Gly Gly Val Gly Phe Lys Ile
           530                 535                 540

Ile Asn Thr Ala Ser Ile Gln Ser Leu Ile Cys Asn Asn Val Lys Gly
545                 550                 555                 560

Cys Pro Phe Thr Ala Phe Ser Val Gln Asp Gly Gln Leu Thr Lys Thr
           565                 570                 575

Val Thr Ile Asn Ala Ser Ser Ser His Ser Gly Leu Asp Asp Ile Asn
           580                 585                 590

Pro Thr Val Leu Leu Lys Glu Arg Ser Thr Glu Leu
           595                 600

<210> SEQ ID NO 6
<211> LENGTH: 3509
<212> TYPE: DNA
<213> ORGANISM: Canis familiaris

<400> SEQUENCE: 6
atggaaacag tcaaaaattt attttagaag agatttttca ttcttagata gtataaaaat      60
aaacaggcat ttgttaacac ttacatctta cataagttaa tttaaataca catttgtctg     120
aggcaccaaa acattcatat attatactcc gaattcagtc ggctttgata ttaataacaa     180
aatttctttc agtgaagtta aaaaggtttt tacataagcc cttctaatat tgactatttc     240 ttaactttt aaacataaaa tcttaaaaat tcccctgagt tatttccttt aataaaattt     300
cattttcttt ctctacctaa agacatgctt tctcatttac aaatactgat gttatctgta     360
atcaagtgca tgatttaaaa atattaagaa tccacaaaaa atattaaaac ccacaagtga     420
tatttgcacc tgtgtcctca ataagttata gctgaatgac ttaatgaagg atycatargt     480
ccctcaaaac tgtaaagatc ttatggtaca tgcaggttaa tgagacacag tgttctctgt     540
gggctggtat atagggaaat ctatatttca attccaactt gccatatttc aatataccag     600
agttgggttc ctgaaaattt actcacagat ctcaaataat ttctcttagt gtttacataa     660
taattcagag ttaatctcaa agaagatata ctgattctca cataatgcaa aaaaaaaaa     720 aatgattgca gcttaaacct agtttataat aacatcctaa caaacaaat aataatcctc     780 aataaattaa gtatacagta ccagcaaatg tcagctgaca atgagatgtg aaaagaaac     840 attatcttcc cgggaactat tcagaatttg actttgcttt taaatgagaa aggatattct     900
taatagaaat acgacttcct tccatcaaga accccctaca gttctttgtc agtcattagc     960
ctcattgaag ccttctgtta caatttaaaa ttaatttaca aaaagatcgc tgcctttcac    1020
ttaaaataag tgtatactgt tgtgtataga gtcctttaag ggctgttttt tttttccttt    1080
cattcctctt aagaggagct aaattactag tagtcctgag ttgaggtttt cctgaaaact    1140
tacacaagtt caggtaagaa agtatagaca gagtccaaag aaaggtatac tcagatctta    1200
aaaatcaagg aaacaagaaa gtaaactgat cagaagagag tttctaccag cacagtggct    1260
aacagaagaa aagaaagtgt gcaggtagtt gcttctaatg caccagggaa gatacactag    1320
aaatcccgat agtgtcgaaa aaaacttgca gcattttgtc atcctggaac agcatttaaa    1380

-continued

```
tatccaacat cttcgctttt gttcataata ataatataaa ctgaaattca agtaaaagga      1440
tgtcaaactc atttataaaa cagaaaactg ttttcctctt taacccgaag acatctttaa      1500
aatagtgaca tgaaaatctt cacaagtatg accccttttct ccttaacaga tgttaagtaa     1560
cataaggagt ttaacataaa tattaaataa ttaagttaaa aggaatcgtc catataaata      1620
aataaatagg attaacaggc ttctatagtt cagttgaccg ttctttcagt aggactgtgg      1680
gattgatgtc atctagaccg gagtgcgaag agcttgcatt aatggtgact gttttggtga      1740
gttgtccgtc ttgaacagag aatgcagtga atggacagcc cttcacgtta ttgcagatga      1800
gagactggat tgaggcagtg ttgatgattt taaagcctac ttctccacca aaggtgctag      1860
gcttccagta gtcaggtgaa cagatgggat tacccataag tcctttcaag gagaatggtg      1920
ctcccatttc taccatggtc tcaccaaaga tggcatctgg acgaggcttt tctaccaaga      1980
gggcaggata cagctccatg gcatcaatat caccataaag ggcctccaac cccgcagcca      2040
tttccttctc tcctgtaagt tcttcgaatg atgtataggg cttcagccta aagcgtttgc      2100
gatactcatt aagagactgg tatttcatct gtctgctctg gtcaatcgaa gcttttgcta      2160
cttgttgtac tgcagctgga acattcctgc caccggcaac cctgccagca atttgcctgc      2220
tgaatgattc cacaaactgg gtaaggccat gttccaataa tatagagttg ttgtagataa      2280
actgttggaa attgtactcc tggtcatcta tttgcaaggt gtcaggcagg aggggatgcc      2340
agtggtagag tgtgttaaac tcagcagcaa tgcggttttg gtactggaat gttggttga      2400 aaagcagctc tgggtcaaac ttcagcttga agtgatagcc actcaagtgt tgtacatagt      2460
cttcaatcac aatcttaatg gtttctccta taagtattag cctgctcgtc tggaataacc      2520
gctcatcatc ccattctggg tgctcctgtt taagcacatc acacactctg ttatgctccc      2580
gcagccaaat ggtggcatac atcatcagac caggcaccag accaaagacc tcctggccca      2640
cagcaaactg caggtgttca ggaacatgag gtgggtagat catctcgacc tgagtatctt      2700
tgacggtagg aggatacacc tctccatcaa ttacctgata tttcattttt ccatccttga      2760
aaaggcgcag tttatgttgt ctatccaaag tttccccata acatgatttt aagtccaccc      2820
catggcccaa tcctttggtg aaagctggtc ctcgcttatg atctgtcttg aaaaattgat      2880
gggtaaagtg ctgggcaaag aatgcaaaca tcatattggt gccttgggga tcaggaatga      2940
actttcttcg cagaagaaac ttttccacaa tctcttttga atcaggaagc tctttcttgc      3000
ctttcacacc catgggtgtt ggacagtcat caggtacagg gggaagagct ctggtataat      3060
aggagaggtt agaaaaggct tcccagcttt tatagccgta gttcacatta taagttggtg      3120
gactctcaat caaatgtgac cgggatgtca acacatattt cataattgta tttcgcagga      3180
aggggatgtt attgacaatg ttccagactc ccttgaagtg ggtaagtatg tagtgtactg      3240
tatttggagt gggtttcagg tataatttta ttcttgtcag aaattccggt gttgagcagt      3300
tttcgccgta gaatcctgtt cgggtacagt cacacttata ctggtcaaat cctgtgctca      3360
tacaaatacc ttggttttga catgggtggg aacagcaagg atttgctgcg cggacgaccg      3420
ccagggcggc gcagagcacc agggcgcggg ccagcatcgc ggcggcgggc ggggcgcggg      3480
cggagcgcgg gcggtggcag aggcggcgg                                        3509
```

```
<210> SEQ ID NO 7
<211> LENGTH: 1812
<212> TYPE: DNA
<213> ORGANISM: Canis familiaris

<400> SEQUENCE: 7
```

```
atgctggccc gcgccctggt gctctgcgcc gccctggcgg tcgtccgcgc agcaaatcct      60
tgctgttccc acccatgtca aaaccaaggt atttgtatga gcacaggatt tgaccagtat     120
aagtgtgact gtacccgaac aggattctac ggcgaaaact gctcaacacc ggaatttctg     180
acaagaataa aattatacct gaaacccact ccaaatacag tacactacat acttacccac     240
ttcaagggag tctggaacat tgtcaataac atcccttcc tgcgaaatac aattatgaaa      300
tatgtgttga catcccggtc acatttgatt gagagtccac caacttataa tgtgaactac     360
ggctataaaa gctgggaagc cttttctaac ctctcctatt ataccagagc tcttcccccc t    420 gtacctgatg actgtccaac acccatgggt gtgaaaggca agaaagagct tcctgattca     480
aaagagattg tggaaaagtt tcttctgcga agaaagttca ttcctgatcc caaggcacc      540 aatatgatgt ttgcattctt tgcccagcac tttacccatc aattttttcaa gacagatcat    600 aagcgaggac cagcttttcac caaaggattg ggccatgggg tggacttaaa tcatgtttat    660
ggggaaactt tggatagaca acataaactg cgccttttca aggatggaaa aatgaaatat     720
caggtaattg atggagaggt gtatcctcct accgtcaaag atactcaggt cgagatgatc    780
tacccacctc atgttcctga acacctgcag tttgctgtgg gccaggaggt ctttggtctg     840
gtgcctggtc tgatgatgta tgccaccatt tggctgcggg agcataacag agtgtgtgat    900
gtgcttaaac aggagcaccc agaatgggat gatgagcggt tattccagac gagcaggcta    960
atacttatag gagaaaccat taagattgtg attgaagact atgtacaaca cttgagtggc    1020
tatcacttca agctgaagtt tgacccgagag ctgcttttca accaacaatt ccagtaccaa   1080
aaccgcattg ctgctgagtt taacacactc taccactggc atccctcct gcctgacacc    1140 ttgcaaatag atgaccagga gtacaatttc aacagttta tctacaacaa ctctatatta     1200
ttggaacatg gccttaccca gtttgtggaa tcattcagca ggcaaattgc tggcagggtt    1260
gccggtggca ggaatgttcc agctgcagta caacaagtag caaaagcttc gattgaccag    1320
agcagacaga tgaaatacca gtctcttaat gagtatcgca aacgctttag gctgaagccc    1380
tatacatcat tcgaagaact acaggagag aaggaaatgg ctgcggggtt ggaggccctt    1440
tatggtgata ttgatgccat ggagctgtat cctgccctct ggtagaaaaa gcctcgtcca    1500
gatgccatct ttggtgagac catggtgaaa atggagcac cattctcctt gaaaggactt    1560
atgggtaatc ccatctgttc acctgactac tggaagccta gcacctttgg tggagaagta    1620
ggctttaaaa tcatcaacac tgcctcaatc cagtctctca tctgcaataa cgtgaagggc    1680
tgtccattca ctgcattctc tgttcaagac ggacaactca ccaaaacagt caccattaat    1740
gcaagctctt cgcactccgg tctagatgac atcaatccca cagtcctact gaaagaacgg    1800
tcaactgaac ta                                                        1812
```

<210> SEQ ID NO 8
<211> LENGTH: 1812
<212> TYPE: DNA
<213> ORGANISM: Canis familiaris

<400> SEQUENCE: 8

```
tagttcagtt gaccgttctt tcagtaggac tgtgggattg atgtcatcta gaccggagtg     60
cgaagagctt gcattaatgg tgactgtttt ggtgagttgt ccgtcttgaa cagagaatgc    120
agtgaatgga cagcccttca cgttattgca gatgagagac tggattgagg cagtgttgat   180
gattttaaag cctacttctc caccaaaggt gctaggcttc cagtagtcag gtgaacagat    240
```

```
gggattaccc ataagtcctt tcaaggagaa tggtgctccc atttctacca tggtctcacc    300
aaagatggca tctggacgag gcttttctac caagagggga ggatacagct ccatggcatc    360
aatatcacca taaagggcct ccaaccccgc agccatttcc ttctctcctg taagttcttc    420
gaatgatgta tagggcttca gcctaaagcg tttgcgatac tcattaagag actggtattt    480
catctgtctg ctctggtcaa tcgaagcttt tgctacttgt tgtactgcag ctggaacatt    540
cctgccaccg gcaaccctgc cagcaatttg cctgctgaat gattccacaa actgggtaag    600
gccatgttcc aataatatag agttgttgta gataaactgt tggaaattgt actcctggtc    660
atctatttgc aaggtgtcag gcaggagggg atgccagtgg tagagtgtgt taaactcagc    720
agcaatgcgg ttttggtact ggaattgttg gttgaaaagc agctctgggt caaacttcag    780
cttgaagtga tagccactca agtgttgtac atagtcttca atcacaatct taatggtttc    840
tcctataagt attagcctgc tcgtctggaa taaccgctca tcatcccatt ctgggtgctc    900
ctgtttaagc acatcacaca ctctgttatg ctcccgcagc caaatggtgg catacatcat    960
cagaccaggc accagaccaa agacctcctg cccacagca  aactgcaggt gttcaggaac   1020
atgaggtggg tagatcatct cgacctgagt atctttgacg gtaggaggat acacctctcc   1080
atcaattacc tgatatttca ttttttccatc cttgaaaagg cgcagtttat gttgtctatc   1140 caaagttttcc ccataaacat gatttaagtc caccccatgg cccaatcctt tggtgaaagc   1200
tggtcctcgc ttatgatctg tcttgaaaaa ttgatgggta aagtgctggg caaagaatgc   1260
aaacatcata ttggtgcctt ggggatcagg aatgaacttt cttcgcagaa gaaacttttc   1320
cacaatctct tttgaatcag gaagctcttt cttgcctttc acacccatgg gtgttggaca   1380
gtcatcaggt acaggggggaa gagctctggt ataataggag aggttagaaa aggcttccca   1440
gcttttatag ccgtagttca cattataagt tggtggactc tcaatcaaat gtgaccggga   1500
tgtcaacaca tatttcataa ttgtatttcg caggaagggg atgttattga caatgttcca   1560
gactcccttg aagtgggtaa gtatgtagtg tactgtatt  ggagtgggtt tcaggtataa   1620
ttttattctt gtcagaaatt ccggtgttga gcagttttcg ccgtagaatc ctgttcgggt   1680
acagtcacac ttatactggt caaatcctgt gctcatacaa ataccttggt tttgacatgg   1740
gtgggaacag caaggatttg ctgcgcggac gaccgccagg gcggcgcaga gcaccagggc   1800
gcgggccagc at                                                       1812

<210> SEQ ID NO 9
<211> LENGTH: 275
<212> TYPE: DNA
<213> ORGANISM: Canis familiaris
<220> FEATURE:
<221> NAME/KEY: CDS
<222> LOCATION: (1)..(273)
<223> OTHER INFORMATION:

<400> SEQUENCE: 9 ttt gca caa cac ttc acc cac cag ttc ttc aaa act tct ggc aag atg    48
Phe Ala Gln His Phe Thr His Gln Phe Phe Lys Thr Ser Gly Lys Met
1               5                   10                  15 ggt cct ggc ttc acc aag gcc ttg ggc cat ggg gta gat ctt ggt cac    96
Gly Pro Gly Phe Thr Lys Ala Leu Gly His Gly Val Asp Leu Gly His
            20                  25                  30 att tat ggg gac aat ctg gac cgt cag tat cag ctg cgg ctc ttt aag   144
Ile Tyr Gly Asp Asn Leu Asp Arg Gln Tyr Gln Leu Arg Leu Phe Lys
        35                  40                  45 gat ggg aaa ctc aag tat cag gtt ctg gat gga gag atg tac ccg tca   192
```

```
Asp Gly Lys Leu Lys Tyr Gln Val Leu Asp Gly Glu Met Tyr Pro Ser
 50                  55                  60 tct gtg gag gag gcg cct gtg ttg atg cac tac cca cgg ggc att ctg      240
Ser Val Glu Glu Ala Pro Val Leu Met His Tyr Pro Arg Gly Ile Leu
 65                  70                  75                  80 ccc cag agt cag atg gct gtg ggc cag gag gtg tt                       275
Pro Gln Ser Gln Met Ala Val Gly Gln Glu Val
                 85                  90

<210> SEQ ID NO 10
<211> LENGTH: 91
<212> TYPE: PRT
<213> ORGANISM: Canis familiaris

<400> SEQUENCE: 10

Phe Ala Gln His Phe Thr His Gln Phe Phe Lys Thr Ser Gly Lys Met
 1               5                  10                  15

Gly Pro Gly Phe Thr Lys Ala Leu Gly His Gly Val Asp Leu Gly His
                 20                  25                  30

Ile Tyr Gly Asp Asn Leu Asp Arg Gln Tyr Gln Leu Arg Leu Phe Lys
             35                  40                  45

Asp Gly Lys Leu Lys Tyr Gln Val Leu Asp Gly Glu Met Tyr Pro Ser
 50                  55                  60

Ser Val Glu Glu Ala Pro Val Leu Met His Tyr Pro Arg Gly Ile Leu
 65                  70                  75                  80

Pro Gln Ser Gln Met Ala Val Gly Gln Glu Val
                 85                  90

<210> SEQ ID NO 11
<211> LENGTH: 275
<212> TYPE: DNA
<213> ORGANISM: Canis familiaris

<400> SEQUENCE: 11
aacacctcct ggcccacagc catctgactc tggggcagaa tgccccgtgg gtagtgcatc     60
aacacaggcg cctcctccac agatgacggg tacatctctc catccagaac ctgatacttg    120
agtttcccat ccttaaagag ccgcagctga tactgacggt ccagattgtc cccataaatg    180
tgaccaagat ctaccccatg gcccaaggcc ttggtgaagc caggaccat cttgccagaa     240 gttttgaaga actggtgggt gaagtgttgt gcaaa                               275

<210> SEQ ID NO 12
<211> LENGTH: 2693
<212> TYPE: DNA
<213> ORGANISM: Canis familiaris
<220> FEATURE:
<221> NAME/KEY: CDS
<222> LOCATION: (31)..(1929)
<223> OTHER INFORMATION:

<400> SEQUENCE: 12
gcaccccgag cgcagcagcc gcccagagct atg agc cgt gag ttc gac cct gag      54
                                 Met Ser Arg Glu Phe Asp Pro Glu
                                  1               5 gcc ccc agg aac cct ctt cgc ctc ccg ggg gag cct cga atg cca ggc      102
Ala Pro Arg Asn Pro Leu Arg Leu Pro Gly Glu Pro Arg Met Pro Gly
         10                  15                  20 cca gcc ctc acc tct cgc tcc gca ggg ggt agt cgc ctg cac cgg tgg      150
Pro Ala Leu Thr Ser Arg Ser Ala Gly Gly Ser Arg Leu His Arg Trp
 25                  30                  35                  40
```

```
ccg ctg ctc ctg ctg ctg ctg ctg ctg ccg ccg ccc ccg gtc ctg          198
Pro Leu Leu Leu Leu Leu Leu Leu Leu Pro Pro Pro Pro Val Leu
                45                  50                  55 ccc gcg gaa gcc cgg acc ccg gcg cct gtg aac ccg tgt tgt tac tac      246
Pro Ala Glu Ala Arg Thr Pro Ala Pro Val Asn Pro Cys Cys Tyr Tyr
            60                  65                  70 cca tgt cag cac caa ggg atc tgt gtc cgc ttc ggc ctt gac cgc tac      294
Pro Cys Gln His Gln Gly Ile Cys Val Arg Phe Gly Leu Asp Arg Tyr
        75                  80                  85 cag tgt gac tgc acc cgc acg ggc tat tct ggc ccc aac tgc acc atc      342
Gln Cys Asp Cys Thr Arg Thr Gly Tyr Ser Gly Pro Asn Cys Thr Ile
    90                  95                  100 ccc gag ctg tgg acc tgg ctc cgg aat tca ctg cgc ccc agt ccc tct      390
Pro Glu Leu Trp Thr Trp Leu Arg Asn Ser Leu Arg Pro Ser Pro Ser
105                 110                 115                 120 ttc ctc cac ttc ctg ctg acg cat ggg cgc tgg ttt tgg gaa ttc atc      438
Phe Leu His Phe Leu Leu Thr His Gly Arg Trp Phe Trp Glu Phe Ile
            125                 130                 135 aat gcc acc ttc atc cgt gac atg ctc atg cgt ctg gta ctc aca gcg      486
Asn Ala Thr Phe Ile Arg Asp Met Leu Met Arg Leu Val Leu Thr Ala
        140                 145                 150 cgt tcc aac ctt atc ccc agt cct ccc acc tac aac ata gcg cat gac      534
Arg Ser Asn Leu Ile Pro Ser Pro Pro Thr Tyr Asn Ile Ala His Asp
    155                 160                 165 tac atc agc tgg gag tcc ttc tcc aat gtg agc tat tac act cgt gtt      582
Tyr Ile Ser Trp Glu Ser Phe Ser Asn Val Ser Tyr Tyr Thr Arg Val
170                 175                 180 ctg ccc tct gtg ccc caa gat tgc ccc acg ccc atg ggg acc aaa ggg      630
Leu Pro Ser Val Pro Gln Asp Cys Pro Thr Pro Met Gly Thr Lys Gly
185                 190                 195                 200 aag aag cag ttg cca gac gcc caa ctc ctg ggc cgt cgc ttc ctg ctc      678
Lys Lys Gln Leu Pro Asp Ala Gln Leu Leu Gly Arg Arg Phe Leu Leu
            205                 210                 215 agg agg aag ttc ata cct gac ccc caa ggc acc aac ctc atg ttc gcc      726
Arg Arg Lys Phe Ile Pro Asp Pro Gln Gly Thr Asn Leu Met Phe Ala
        220                 225                 230 ttc ttt gca caa cac ttc acc cat cag ttc ttc aaa act tct ggc aag      774
Phe Phe Ala Gln His Phe Thr His Gln Phe Phe Lys Thr Ser Gly Lys
    235                 240                 245 atg ggt cct ggc ttc acc aag gcc ttg ggc cat ggg gta gat ctt ggc      822
Met Gly Pro Gly Phe Thr Lys Ala Leu Gly His Gly Val Asp Leu Gly
250                 255                 260 cac att tat ggg gac aat ctg gac cgt cag tat cag ctg cgg ctc ttt      870
His Ile Tyr Gly Asp Asn Leu Asp Arg Gln Tyr Gln Leu Arg Leu Phe
265                 270                 275                 280 aag gat ggg aaa ctc aag tat cag gtt ctg gat gga gag atg tac ccg      918
Lys Asp Gly Lys Leu Lys Tyr Gln Val Leu Asp Gly Glu Met Tyr Pro
            285                 290                 295 cca tct gtg gag gag gcg cct gtg ttg atg cac tac cca cgg ggc att      966
Pro Ser Val Glu Glu Ala Pro Val Leu Met His Tyr Pro Arg Gly Ile
        300                 305                 310 ctg ccc cag agt cag atg gcc gtg ggc cag gag gtg ttt ggg ctg ctt     1014
Leu Pro Gln Ser Gln Met Ala Val Gly Gln Glu Val Phe Gly Leu Leu
    315                 320                 325 cct ggg ctc atg ctc tat gcc acg ctc tgg ctc cgt gag cac aat cgt     1062
Pro Gly Leu Met Leu Tyr Ala Thr Leu Trp Leu Arg Glu His Asn Arg
330                 335                 340 gtg tgt gac ctg ctg aag gct gag cac ccc act tgg ggt gat gag caa     1110
Val Cys Asp Leu Leu Lys Ala Glu His Pro Thr Trp Gly Asp Glu Gln
345                 350                 355                 360
```

-continued

| | |
|---|---|
| ctc ttc cag acg gcc cga ctc atc ctc att ggg gag acc atc aag att<br>Leu Phe Gln Thr Ala Arg Leu Ile Leu Ile Gly Glu Thr Ile Lys Ile<br>            365                  370                375 | 1158 |
| gtg att gag gag tat gtg cag cag ctg agt ggc tac ttc ttg cag ctg<br>Val Ile Glu Glu Tyr Val Gln Gln Leu Ser Gly Tyr Phe Leu Gln Leu<br>        380                  385                390 | 1206 |
| aag ttc gac ccg gag ctg ctg ttt agc gcc cag ttc cag tac cgc aac<br>Lys Phe Asp Pro Glu Leu Leu Phe Ser Ala Gln Phe Gln Tyr Arg Asn<br>395                  400                405 | 1254 |
| cgc atc gcc atg gag ttc aac cag ctg tac cac tgg cac ccg ctc atg<br>Arg Ile Ala Met Glu Phe Asn Gln Leu Tyr His Trp His Pro Leu Met<br>410                  415                420 | 1302 |
| cca gac tcc ttc tgg gtg ggt tcc cag gag tac agc tat gag cag ttc<br>Pro Asp Ser Phe Trp Val Gly Ser Gln Glu Tyr Ser Tyr Glu Gln Phe<br>425                  430                435              440 | 1350 |
| ctg ttc aac acc tcc atg ctg acg cac tac ggg atc gag gcc ctg gtg<br>Leu Phe Asn Thr Ser Met Leu Thr His Tyr Gly Ile Glu Ala Leu Val<br>        445                  450                455 | 1398 |
| gat gcc ttc tct cgc cag agc gcc ggc cgg att ggt gga ggt aga aac<br>Asp Ala Phe Ser Arg Gln Ser Ala Gly Arg Ile Gly Gly Gly Arg Asn<br>            460                  465                470 | 1446 |
| ata gac cac cat gtc ctg cac gtg gct gtg gaa acc atc aag gaa tcc<br>Ile Asp His His Val Leu His Val Ala Val Glu Thr Ile Lys Glu Ser<br>                475                480              485 | 1494 |
| cgc gag ttg cgg ctg cag ccc ttc aat gag tac cgc aag agg ttt ggc<br>Arg Glu Leu Arg Leu Gln Pro Phe Asn Glu Tyr Arg Lys Arg Phe Gly<br>        490                  495                500 | 1542 |
| atg agg ccc tac atg tcc ttc cag gaa ctc aca ggg gag aag gag atg<br>Met Arg Pro Tyr Met Ser Phe Gln Glu Leu Thr Gly Glu Lys Glu Met<br>505                  510                515              520 | 1590 |
| gca gcc gag ttg gag gag ctg tat gga gac att gat gcc ttg gaa ttc<br>Ala Ala Glu Leu Glu Glu Leu Tyr Gly Asp Ile Asp Ala Leu Glu Phe<br>                525                530              535 | 1638 |
| tac ccg ggg ctt ctt ctg gag aag tgc cat cca aac tcc atc ttt gga<br>Tyr Pro Gly Leu Leu Leu Glu Lys Cys His Pro Asn Ser Ile Phe Gly<br>            540                  545                550 | 1686 |
| gag agt atg ata gaa att ggg gct ccc ttc tcc ctt aag ggc ctc cta<br>Glu Ser Met Ile Glu Ile Gly Ala Pro Phe Ser Leu Lys Gly Leu Leu<br>                555                560              565 | 1734 |
| ggg aat ccc atc tgt tct cca gag tac tgg aag cca agc aca ttc ggt<br>Gly Asn Pro Ile Cys Ser Pro Glu Tyr Trp Lys Pro Ser Thr Phe Gly<br>570                  575                580 | 1782 |
| ggt gag atg ggc ttc aat atg gtc aag aca gcc aca ctg aag aag ctg<br>Gly Glu Met Gly Phe Asn Met Val Lys Thr Ala Thr Leu Lys Lys Leu<br>585                  590                595              600 | 1830 |
| gtc tgc ctt aac acc aag act tgt ccc tat gtt tcc ttc cgt gtg cct<br>Val Cys Leu Asn Thr Lys Thr Cys Pro Tyr Val Ser Phe Arg Val Pro<br>                605                610              615 | 1878 |
| gac ccc cac cag gat ggc ggg cct ggt gtg gag cgg ccg tcc aca gag<br>Asp Pro His Gln Asp Gly Gly Pro Gly Val Glu Arg Pro Ser Thr Glu<br>        620                  625                630 | 1926 |
| ctc tgagggggca gagcagcagc attctggagg gtggacttgt catcccagaa<br>Leu | 1979 |
| tgctgaggct ggggttaata atcccaaatg ttgggtcttt ggtttgcctc aagaatatca | 2039 |
| aggtcaacat ttagaacttt gtgtctctca cccattatct ggaatatcat ggtcttgttt | 2099 |
| gttattctag aatgctgaat tcctggttga ccatctagaa tggatggagt gatgcttctt | 2159 |
| tggcaagcca gaacactggt tcctggccga caacctagaa tgtcagactt ctggttgact | 2219 |

```
taagacgtag gcattctcta atgtgaagct cctgacagaa tcatctagaa agatagggga       2279
ttcttatttt gcattctaga attctgggca gccctccagc atgttgattt ttttcactgg       2339
cagttcagaa tgttgtgctc ttgattgctg atccaaaata gtggctggta tgccagatca       2399
gtcttgctct gaatgcctag aatggtaatt tgattcattt tcctgttcag tgagataccc       2459
ccaaagcagg agaatctaca gcctaaccag agtgcattgc ctgcctctgt gcctgcccca       2519
aggacttagg gggcagagtg ttcttcctgg gatgctgact cagaccctgg tccaaggaga       2579
tagaacaggt gggctttttc caggtcattg gttggaggcc accagagctc tgttgccatc       2639
tttgtcttga ctcatgacag ctgtttctca tgaaactaat aaaatttttt ttcc             2693
```

<210> SEQ ID NO 13
<211> LENGTH: 633
<212> TYPE: PRT
<213> ORGANISM: Canis familiaris

<400> SEQUENCE: 13

```
Met Ser Arg Glu Phe Asp Pro Glu Ala Pro Arg Asn Pro Leu Arg Leu
1               5                   10                  15

Pro Gly Glu Pro Arg Met Pro Gly Pro Ala Leu Thr Ser Arg Ser Ala
                20                  25                  30

Gly Gly Ser Arg Leu His Arg Trp Pro Leu Leu Leu Leu Leu Leu Leu
            35                  40                  45

Leu Leu Pro Pro Pro Pro Val Leu Pro Ala Glu Ala Arg Thr Pro Ala
        50                  55                  60

Pro Val Asn Pro Cys Cys Tyr Tyr Pro Cys Gln His Gln Gly Ile Cys
65                  70                  75                  80

Val Arg Phe Gly Leu Asp Arg Tyr Gln Cys Asp Cys Thr Arg Thr Gly
                85                  90                  95

Tyr Ser Gly Pro Asn Cys Thr Ile Pro Glu Leu Trp Thr Trp Leu Arg
                100                 105                 110

Asn Ser Leu Arg Pro Ser Pro Ser Phe Leu His Phe Leu Leu Thr His
            115                 120                 125

Gly Arg Trp Phe Trp Glu Phe Ile Asn Ala Thr Phe Ile Arg Asp Met
        130                 135                 140

Leu Met Arg Leu Val Leu Thr Ala Arg Ser Asn Leu Ile Pro Ser Pro
145                 150                 155                 160

Pro Thr Tyr Asn Ile Ala His Asp Tyr Ile Ser Trp Glu Ser Phe Ser
                165                 170                 175

Asn Val Ser Tyr Tyr Thr Arg Val Leu Pro Ser Val Pro Gln Asp Cys
                180                 185                 190

Pro Thr Pro Met Gly Thr Lys Gly Lys Lys Gln Leu Pro Asp Ala Gln
            195                 200                 205

Leu Leu Gly Arg Arg Phe Leu Leu Arg Arg Lys Phe Ile Pro Asp Pro
        210                 215                 220

Gln Gly Thr Asn Leu Met Phe Ala Phe Phe Ala Gln His Phe Thr His
225                 230                 235                 240

Gln Phe Phe Lys Thr Ser Gly Lys Met Gly Pro Gly Phe Thr Lys Ala
                245                 250                 255

Leu Gly His Gly Val Asp Leu Gly His Ile Tyr Gly Asp Asn Leu Asp
                260                 265                 270

Arg Gln Tyr Gln Leu Arg Leu Phe Lys Asp Gly Lys Leu Lys Tyr Gln
            275                 280                 285
```

```
Val Leu Asp Gly Glu Met Tyr Pro Pro Ser Val Glu Ala Pro Val
    290                 295                 300

Leu Met His Tyr Pro Arg Gly Ile Leu Pro Gln Ser Gln Met Ala Val
305                 310                 315                 320

Gly Gln Glu Val Phe Gly Leu Leu Pro Gly Leu Met Leu Tyr Ala Thr
                325                 330                 335

Leu Trp Leu Arg Glu His Asn Arg Val Cys Asp Leu Leu Lys Ala Glu
                340                 345                 350

His Pro Thr Trp Gly Asp Glu Gln Leu Phe Gln Thr Ala Arg Leu Ile
                355                 360                 365

Leu Ile Gly Glu Thr Ile Lys Ile Val Ile Glu Glu Tyr Val Gln Gln
370                 375                 380

Leu Ser Gly Tyr Phe Leu Gln Leu Lys Phe Asp Pro Glu Leu Leu Phe
385                 390                 395                 400

Ser Ala Gln Phe Gln Tyr Arg Asn Arg Ile Ala Met Glu Phe Asn Gln
                405                 410                 415

Leu Tyr His Trp His Pro Leu Met Pro Asp Ser Phe Trp Val Gly Ser
                420                 425                 430

Gln Glu Tyr Ser Tyr Glu Gln Phe Leu Phe Asn Thr Ser Met Leu Thr
                435                 440                 445

His Tyr Gly Ile Glu Ala Leu Val Asp Ala Phe Ser Arg Gln Ser Ala
450                 455                 460

Gly Arg Ile Gly Gly Gly Arg Asn Ile Asp His His Val Leu His Val
465                 470                 475                 480

Ala Val Glu Thr Ile Lys Glu Ser Arg Glu Leu Arg Leu Gln Pro Phe
                485                 490                 495

Asn Glu Tyr Arg Lys Arg Phe Gly Met Arg Pro Tyr Met Ser Phe Gln
                500                 505                 510

Glu Leu Thr Gly Glu Lys Glu Met Ala Ala Glu Leu Glu Glu Leu Tyr
                515                 520                 525

Gly Asp Ile Asp Ala Leu Glu Phe Tyr Pro Gly Leu Leu Leu Glu Lys
530                 535                 540

Cys His Pro Asn Ser Ile Phe Gly Glu Ser Met Ile Glu Ile Gly Ala
545                 550                 555                 560

Pro Phe Ser Leu Lys Gly Leu Leu Gly Asn Pro Ile Cys Ser Pro Glu
                565                 570                 575

Tyr Trp Lys Pro Ser Thr Phe Gly Gly Glu Met Gly Phe Asn Met Val
                580                 585                 590

Lys Thr Ala Thr Leu Lys Lys Leu Val Cys Leu Asn Thr Lys Thr Cys
                595                 600                 605

Pro Tyr Val Ser Phe Arg Val Pro Asp Pro His Gln Asp Gly Gly Pro
                610                 615                 620

Gly Val Glu Arg Pro Ser Thr Glu Leu
625                 630
```

<210> SEQ ID NO 14
<211> LENGTH: 2693
<212> TYPE: DNA
<213> ORGANISM: Canis familiaris

<400> SEQUENCE: 14
ggaaaaaaaa ttttattagt ttcatgagaa acagctgtca tgagtcaaga caaagatggc    60
aacagagctc tggtggcctc caaccaatga cctggaaaaa gcccaccgt tctatctcct    120 tggaccaggg tctgagtcag catcccagga agaacactct gcccctaag tccttgggc    180

```
aggcacagag gcaggcaatg cactctggtt aggctgtaga ttctcctgct ttggggtat    240 ctcactgaac aggaaaatga atcaaattac cattctaggc attcagagca agactgatct    300
ggcataccag ccactatttt ggatcagcaa tcaagagcac aacattctga actgccagtg    360
aaaaaaatca acatgctgga gggctgccca gaattctaga atgcaaaata agaatcccct    420
atctttctag atgattctgt caggagcttc acattagaga atgcctacgt cttaagtcaa    480
ccagaagtct gacattctag gttgtcggcc aggaaccagt gttctggctt gccaaagaag    540
catcactcca tccattctag atggtcaacc aggaattcag cattctagaa taacaaacaa    600
gaccatgata ttccagataa tgggtgagag acacaaagtt ctaaatgttg accttgatat    660
tcttgaggca aaccaaagac ccaacatttg ggattattaa ccccagcctc agcattctgg    720
gatgacaagt ccaccctcca gaatgctgct gctctgcccc ctcagagctc tgtggacggc    780
cgctccacac caggcccgcc atcctggtgg gggtcaggca cacggaagga aacataggga    840
caagtcttgg tgttaaggca gaccagcttc ttcagtgtgg ctgtcttgac catattgaag    900
cccatctcac caccgaatgt gcttggcttc cagtactctg agaacagat gggattccct     960 aggaggccct aagggagaa gggagcccca atttctatca tactctctcc aaagatggag    1020
tttggatggc acttctccag aagaagcccc gggtagaatt ccaaggcatc aatgtctcca    1080
tacagctcct ccaactcggc tgccatctcc ttctcccctg tgagttcctg gaaggacatg    1140
tagggcctca tgccaaacct cttgcggtac tcattgaagg gctgcagccg caactcgcgg    1200
gattccttga tggtttccac agccacgtgc aggacatggt ggtctatgtt tctacctcca    1260
ccaatccggc cggcgctctg gcgagagaag gcatccacca gggcctcgat cccgtagtgc    1320
gtcagcatgg aggtgttgaa caggaactgc tcatagctgt actcctggga acccacccag    1380
aaggagtctg gcatgagcgg gtgccagtgg tacagctggt tgaactccat ggcgatgcgg    1440
ttgcggtact ggaactgggc gctaaacagc agctcccggt cgaacttcag ctgcaagaag    1500
tagccactca gctgctgcac atactcctca atcacaatct tgatggtctc cccaatgagg    1560
atgagtcggg ccgtctggaa gagttgctca tcaccccaag tggggtgctc agccttcagc    1620
aggtcacaca cacgattgtg ctcacgcagc cagagcgtgg catagagcat gagcccagga    1680
agcagcccaa acacctcctg gcccacggcc atctgactct ggggcagaat gccccgtggg    1740
tagtgcatca acacaggcgc ctcctccaca gatggcgggt acatctctcc atccagaacc    1800
tgatacttga gtttcccatc cttaaagagc cgcagctgat actgacggtc cagattgtcc    1860
ccataaatgt ggccaagatc taccccatgg cccaaggcct tggtgaagcc aggacccatc    1920
ttgccagaag ttttgaagaa ctgatgggtg aagtgttgtg caaagaaggc gaacatgagg    1980
ttggtgcctt gggggtcagg tatgaacttc ctcctgagca ggaagcgacg gcccaggagt    2040
tgggcgtctg gcaactgctt cttcccttt gtccccatgg gcgtggggca atctggggc     2100 acagagggca gaacacgagt gtaatagctc acattggaga aggactccca gctgatgtag    2160
tcatgcgcta tgttgtaggt gggaggactg gggataaggt tggaacgcgc tgtgagtacc    2220
agacgcatga gcatgtcacg gatgaaggtg gcattgatga attcccaaaa ccagcgccca    2280
tgcgtcagca ggaagtggag gaaagaggga ctggggcgca gtgaattccg gagccaggtc    2340
cacagctcgg ggatggtgca gttggggcca gaatagcccg tgcgggtgca gtcacactgg    2400
tagcggtcaa ggccgaagcg gacacagatc ccttggtgct gacatgggta gtaacaacac    2460
gggttcacag gcgccggggt ccgggcttcc gcgggcagga ccgggggcgg cggcagcagc    2520
```

| | | | | |
|---|---|---|---|---|
| agcagcagca | gcaggagcag | cggccaccgg | tgcaggcgac | tccccctgc ggagcgagag | 2580 |
| gtgagggctg | ggcctggcat | tcgaggctcc | cccgggaggc | gaagagggtt cctgggggcc | 2640 |
| tcagggtcga | actcacggct | catagctctg | ggcggctgct | cgctcgggg tgc | 2693 |

<210> SEQ ID NO 15
<211> LENGTH: 1899
<212> TYPE: DNA
<213> ORGANISM: Canis familiaris

<400> SEQUENCE: 15

| | | | | | |
|---|---|---|---|---|---|
| atgagccgtg | agttcgaccc | tgaggccccc | aggaaccctc | ttcgcctccc | gggggagcct | 60 |
| cgaatgccag | gcccagccct | cacctctcgc | tccgcagggg | ggagtcgcct | gcaccggtgg | 120 |
| ccgctgctcc | tgctgctgct | gctgctgctg | ccgccgcccc | cggtcctgcc | cgcggaagcc | 180 |
| cggaccccgg | cgcctgtgaa | cccgtgttgt | tactacccat | gtcagcacca | agggatctgt | 240 |
| gtccgcttcg | gccttgaccg | ctaccagtgt | gactgcaccc | gcacgggcta | ttctggcccc | 300 |
| aactgcacca | tccccgagct | gtggacctgg | ctccggaatt | cactgcgccc | cagtccctct | 360 |
| ttcctccact | tcctgctgac | gcatgggcgc | tggttttggg | aattcatcaa | tgccaccttc | 420 |
| atccgtgaca | tgctcatgcg | tctggtactc | acagcgcgtt | ccaaccttat | ccccagtcct | 480 |
| cccacctaca | acatagcgca | tgactacatc | agctgggagt | ccttctccaa | tgtgagctat | 540 |
| tacactcgtg | ttctgccctc | tgtgccccaa | gattgcccca | cgcccatggg | gaccaaaggg | 600 |
| aagaagcagt | gccagacgc | ccaactcctg | ggccgtcgct | tcctgctcag | gaggaagttc | 660 |
| atacctgacc | cccaaggcac | caacctcatg | ttcgccttct | ttgcacaaca | cttcacccat | 720 |
| cagttcttca | aaacttctgg | caagatgggt | cctggcttca | ccaaggcctt | gggccatggg | 780 |
| gtagatcttg | gccacattta | tggggacaat | ctggaccgtc | agtatcagct | gcggctcttt | 840 |
| aaggatggga | aactcaagta | tcaggttctg | gatggagaga | tgtacccgcc | atctgtggag | 900 |
| gaggcgcctg | tgttgatgca | ctacccacgg | ggcattctgc | cccagagtca | gatggccgtg | 960 |
| ggccaggagg | tgtttgggct | gcttcctggg | ctcatgctct | atgccacgct | ctggctgcgt | 1020 |
| gagcacaatc | gtgtgtgtga | cctgctgaag | gctgagcacc | ccacttgggg | tgatgagcaa | 1080 |
| ctcttccaga | cggcccgact | catcctcatt | ggggagacca | tcaagattgt | gattgaggag | 1140 |
| tatgtgcagc | agctgagtgg | ctacttcttg | cagctgaagt | tcgacccgga | gctgctgttt | 1200 |
| agcgcccagt | tccagtaccg | caaccgcatc | gccatggagt | tcaaccagct | gtaccactgg | 1260 |
| caccccgctca | tgccagactc | cttctgggtg | ggttcccagg | agtacagcta | tgagcagttc | 1320 |
| ctgttcaaca | cctccatgct | gacgcactac | gggatcgagg | ccctggtgga | tgccttctct | 1380 |
| cgccagagcg | ccggccggat | tggtggaggt | agaaacatag | accaccatgt | cctgcacgtg | 1440 |
| gctgtggaaa | ccatcaagga | atcccgcgag | ttgcggctgc | agcccttcaa | tgagtaccgc | 1500 |
| aagaggtttg | gcatgaggcc | ctacatgtcc | ttccaggaac | tcacagggga | gaaggagatg | 1560 |
| gcagccgagt | ggaggagct | gtatggagac | attgatgcct | tggaattcta | cccgggggctt | 1620 |
| cttctggaga | agtgccatcc | aaactccatc | tttggagaga | gtatgataga | aattggggct | 1680 |
| cccttctccc | ttaagggcct | cctagggaat | cccatctgtt | ctccagagta | ctggaagcca | 1740 |
| agcacattcg | tggtgagat | gggcttcaat | atggtcaaga | cagccacact | gaagaagctg | 1800 |
| gtctgcctta | acaccaagac | ttgtccctat | gttccttcc | gtgtgcctga | ccccaccag | 1860 |
| gatggcgggc | tggtgtgga | gcggccgtcc | acagagctc | | | 1899 |

<210> SEQ ID NO 16
<211> LENGTH: 1899
<212> TYPE: DNA
<213> ORGANISM: Canis familiaris

<400> SEQUENCE: 16

```
gagctctgtg acggccgct ccacaccagg cccgccatcc tggtgggggt caggcacacg      60
gaaggaaaca tagggacaag tcttggtgtt aaggcagacc agcttcttca gtgtggctgt    120
cttgaccata ttgaagccca tctcaccacc gaatgtgctt ggcttccagt actctggaga    180
acagatggga ttccctagga ggcccttaag ggagaaggga gccccaattt ctatcatact    240
ctctccaaag atggagtttg atggcacttc tccagaaga agccccgggt agaattccaa     300
ggcatcaatg tctccataca gctcctccaa ctcggctgcc atctccttct ccctgtgag     360
ttcctggaag gacatgtagg gcctcatgcc aaacctcttg cggtactcat tgaagggctg    420
cagccgcaac tcgcgggatt ccttgatggt ttccacagcc acgtgcagga catggtggtc    480
tatgtttcta cctccaccaa tccggccggc gctctggcga gagaaggcat ccaccagggc    540
ctcgatcccg tagtgcgtca gcatggaggt gttgaacagg aactgctcat agctgtactc    600
ctgggaaccc acccagaagg agtctggcat gagcgggtgc cagtggtaca gctggttgaa    660
ctccatggcg atgcggttgc ggtactggaa ctgggcgcta acagcagct ccgggtcgaa     720
cttcagctgc aagaagtagc cactcagctg ctgcacatac tcctcaatca caatcttgat    780
ggtctcccca tgaggatga gtcgggccgt ctggaagagt tgctcatcac cccaagtggg    840
gtgctcagcc ttcagcaggt cacacacacg attgtgctca cgcagccaga gcgtggcata    900
gagcatgagc ccaggaagca gcccaaacac ctcctggccc acggccatct gactctgggg    960
cagaatgccc cgtgggtagt gcatcaacac aggcgcctcc tccacagatg gcgggtacat   1020
ctctccatcc agaacctgat acttgagttt cccatcctta aagagccgca gctgatactg   1080
acggtccaga ttgtccccat aaatgtggcc aagatctacc ccatggccca aggccttggt   1140
gaagccagga cccatcttgc cagaagtttt gaagaactga tgggtgaagt gttgtgcaaa   1200
gaaggcgaac atgaggttgg tgccttgggg gtcaggtatg aacttcctcc tgagcaggaa   1260
gcgacggccc aggagttggg cgtctggcaa ctgcttcttc cctttggtcc ccatgggcgt   1320
ggggcaatct tggggcacag agggcagaac acgagtgtaa tagctcacat tggagaagga   1380
ctcccagctg atgtagtcat gcgctatgtt gtaggtggga ggactgggga taaggttgga   1440
acgcgctgtg agtaccagac gcatgagcat gtcacggatg aaggtggcat tgatgaattc   1500
ccaaaaccag cgcccatgcg tcagcaggaa gtggaggaaa gagggactgg ggcgcagtga   1560
attccggagc caggtccaca gctcggggat ggtgcagttg gggccagaat agcccgtgcg   1620
ggtgcagtca cactggtagc ggtcaaggcc gaagcggaca cagatcccctt ggtgctgaca   1680
tgggtagtaa caacacgggt tcacaggcgc cggggtccgg gcttccgcgg gcaggaccgg   1740
gggcggcggc agcagcagca gcagcagcag gagcagcggc caccggtgca ggcgactccc   1800
ccctgcggag cgagaggtga gggctgggcc tggcattcga ggctccccg ggaggcgaag    1860
agggttcctg ggggcctcag ggtcgaactc acggctcat                          1899
```

<210> SEQ ID NO 17
<211> LENGTH: 18
<212> TYPE: DNA
<213> ORGANISM: Artificial sequence
<220> FEATURE:
<223> OTHER INFORMATION: Synthetic Primer
<220> FEATURE:

<221> NAME/KEY: misc_feature
<222> LOCATION: (9)..(9)
<223> OTHER INFORMATION: n = unknown at position 9

<400> SEQUENCE: 17
twytayggng araaytgy                                                    18

<210> SEQ ID NO 18
<211> LENGTH: 20
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (6)..(6)
<223> OTHER INFORMATION: n = unknown at position 6

<400> SEQUENCE: 18
ccyttnacrt trttrcadat                                                  20

<210> SEQ ID NO 19
<211> LENGTH: 20
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (12)..(12)
<223> OTHER INFORMATION: n = unknown at position 12
<220> FEATURE:
<221> NAME/KEY: misc_feature
<222> LOCATION: (15)..(15)
<223> OTHER INFORMATION: n = unknown at position 15

<400> SEQUENCE: 19
cayttyaarg gngtntggaa                                                  20

<210> SEQ ID NO 20
<211> LENGTH: 21
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (7)..(7)
<223> OTHER INFORMATION: n = unknown at position 7
<220> FEATURE:
<221> NAME/KEY: misc_feature
<222> LOCATION: (10)..(10)
<223> OTHER INFORMATION: n = unknown at position 10

<400> SEQUENCE: 20
ccadatngtn gcrtacatca t                                                21

<210> SEQ ID NO 21
<211> LENGTH: 32
<212> TYPE: DNA
<213> ORGANISM: Artificial sequence
<220> FEATURE:
<223> OTHER INFORMATION: Synthetic Primer

<400> SEQUENCE: 21
aaggatccga tatgctggcc cgcgccctgg tg                                    32

<210> SEQ ID NO 22
<211> LENGTH: 32

```
-continued

<212> TYPE: DNA
<213> ORGANISM: Artificial sequence
<220> FEATURE:
<223> OTHER INFORMATION: Synthetic Primer

<400> SEQUENCE: 22
aagaattccc tagttcagtt gaccgttctt tc                                      32

<210> SEQ ID NO 23
<211> LENGTH: 33
<212> TYPE: DNA
<213> ORGANISM: Artificial sequence
<220> FEATURE:
<223> OTHER INFORMATION: Synthetic Primer

<400> SEQUENCE: 23
aagaattcct atagttcagt tgaccgttct ttc                                     33

<210> SEQ ID NO 24
<211> LENGTH: 24
<212> TYPE: DNA
<213> ORGANISM: Artificial sequence
<220> FEATURE:
<223> OTHER INFORMATION: Synthetic Primer

<400> SEQUENCE: 24
tttgcacaac acttcaccca ccag                                               24

<210> SEQ ID NO 25
<211> LENGTH: 24
<212> TYPE: DNA
<213> ORGANISM: Artificial sequence
<220> FEATURE:
<223> OTHER INFORMATION: Synthetic Primer

<400> SEQUENCE: 25
aaacacctcc tggcccacag ccat                                               24
```

CANINE COX-2 PROTEINS AND USES THEREOF

CROSS-REFERENCE TO RELATED APPLICATIONS

This application is a divisional of U.S. patent application Ser. No. 11/372,770, filed Mar. 10, 2006 now U.S. Pat. No. 7,476,524, entitled "CANINE COX-2 NUCLEIC ACID MOLECULES"; which is a divisional of U.S. patent application Ser. No. 10/679,140, filed Oct. 2, 2003, now issued as U.S. Pat. No. 7,223,578, entitled "CANINE COX-1 NUCLEIC ACID MOLECULES AND FRAGMENTS THEREOF"; which is a divisional of U.S. patent application Ser. No. 09/919,060, filed Jul. 31, 2001, now issued as U.S. Pat. No. 6,638,744 B2, entitled "CANINE COX-2 NUCLEIC ACID MOLECULES AND USES THEREOF"; which claims priority to U.S. Provisional Patent Application Ser. No. 60/224,486, filed Aug. 11, 2000, entitled "CANINE COX-1 AND COX-2 NUCLEIC ACID MOLECULES, PROTEINS AND USES THEREOF"; all of which are incorporated herein by reference.

FIELD OF THE INVENTION

The present invention relates to canine COX-1 and COX-2 nucleic acid molecules, proteins encoded by such nucleic acid molecules, antibodies raised against such proteins, and inhibitors of such proteins. The present invention also includes methods to obtain such proteins, nucleic acid molecules, antibodies, and inhibitory compounds. The present invention also includes therapeutic compositions comprising such inhibitors, as well as uses thereof.

BACKGROUND OF THE INVENTION

Prostaglandins are important mediators of inflammation and are also involved in a cytoprotective role in gastric mucosa. Of particular interest in the present application are the prostaglandin producing enzymes COX-1 and COX-2, also known as prostaglandin H synthase-1 (PGHS-1) and prostaglandin H synthase-2 (PGHS-2). COX-1 is the constitutive isoform and is mainly responsible for the synthesis of cytoprotective prostaglandins in the GI tract whereas COX-2 is inducible and plays a major role in prostaglandin biosynthesis in inflammatory cells and in the central nervous system. Considerable research has been conducted to isolate therapeutic agents which are specific for the inhibition of COX-2, i.e. agents which have the anti-inflammatory benefit of COX-2 inhibition without the GI tract irritation associated with inhibition of COX-1; see, for example, Vane et al., 1998, *Annual Rev. Pharmacol Toxicol.*, 38:97-120; Masferrer et al., 1994, *Proc. Natl. Acad. Sci.*, 91:3228-3232; Vane et al. 1995, *Inflamm. Res.* 44:1-10; Seibert et al., 1994, *Proc. Natl. Acad. Sci.*, 91:12013-12017; and Dubois et al., 1998, *The FASEB Journal*, 12:1063-1072.

Previous research indicates that COX inhibitors can have different selectivity ratios if profiled in assays using cells from different species or sources and it has been postulated that some classes of inhibitors may be species specific in nature; see, for example, Ricketts et al., 1998, *AJVR* 59:1441-1446, Warner et al., 1999, *Proc. Natl. Acad. Sci.*, 96:7563-7568, Laufer et al., 1999, *Inflamm. Res.*, 48:133-138, Giuliano et al., 1999, *British J. Pharmacol*, 126:1824-1830, Riendeau et al., 1997, *Can. J. Physiol. Parmacol.*, 75:1088-1095, Khan et al., 1998, *Toxicologic Pathology*, 26(5): 612-620, and Golden et al., 1999, *Osteoarthritis*, 25(2):359-378. Therefore, isolation and sequencing of canine COX-1 and COX-2 genes may be critical for use in identifying COX-2 specific inhibitors specifically for use in dogs.

Thus, there remains a need to develop COX-2 specific therapeutic agents for use in dogs as well as reagents and methods to identify such therapeutic agents.

SUMMARY OF THE INVENTION

The present invention provides canine COX-1 and COX-2 proteins; nucleic acid molecules encoding canine COX-1 and COX-2 proteins; antibodies raised against such proteins (i.e., anti-canine COX-1 and COX-2 antibodies); mimetopes of such proteins or antibodies; and compounds that inhibit canine COX-2 activity (i.e. inhibitory compounds or inhibitors), particularly those inhibitory compounds that inhibit COX-2 activity but not COX-1 activity (i.e. that specifically inhibit COX-2 activity).

The present invention also includes methods to obtain such proteins, mimetopes, nucleic acid molecules, antibodies and inhibitory compounds. The present invention also includes the use of proteins and antibodies to identify such inhibitory compounds as well as assay kits to identify such inhibitory compounds. Also included in the present invention are therapeutic compositions comprising proteins, mimetopes, nucleic acid molecules, antibodies and inhibitory compounds of the present invention including therapeutic compounds derived from a protein of the present invention that inhibit the activity of canine COX-2 proteins; also included are uses of such therapeutic compounds.

One embodiment of the present invention is an isolated COX-2 nucleic acid molecule that hybridizes with a nucleic acid sequence having SEQ ID NO:1, SEQ ID NO:3, SEQ ID NO:4, SEQ ID NO:6, SEQ ID NO:7, and/or SEQ ID NO:8, under conditions that allow less than or equal to about 10% base pair mismatch and an isolated COX-1 nucleic acid molecule that hybridizes with a nucleic acid sequence having SEQ ID NO:9, SEQ ID NO:11, SEQ ID NO:12, SEQ ID NO:14, SEQ ID NO:15, and/or SEQ ID NO:16 under conditions that allow less than or equal to about 10% base pair mismatch.

Another embodiment of the present invention is an isolated COX-2 nucleic acid molecule having a nucleic acid sequence that is at least about 90% identical to SEQ ID NO:1, SEQ ID NO:3, SEQ ID NO:4, SEQ ID NO:6, SEQ ID NO:7, SEQ ID NO:8, and an isolated COX-1 nucleic acid molecule having a nucleic acid sequence that is at least about 90% identical to SEQ ID NO:9, SEQ ID NO:1, SEQ ID NO:12, SEQ ID NO:14, SEQ ID NO: 15, and/or SEQ ID NO:16.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Another embodiment of the present invention includes an isolated canine COX-2 protein that is at least about 95% identical to an amino acid sequence selected from the group consisting of SEQ ID NO:2, SEQ ID NO:5 and fragments thereof, wherein such fragments can elicit an immune response against respective canine COX-2 proteins or have activity comparable to respective canine COX-2 proteins.

Another embodiment of the present invention includes an isolated canine COX-1 protein that is at least about 95% identical to an amino acid sequence selected from the group consisting of SEQ ID NO:10, SEQ ID NO:13 and fragments thereof, wherein such fragments can elicit an immune response against respective canine COX-1 proteins or have activity comparable to respective canine COX-1 proteins.

Another embodiment of the present invention includes an isolated COX-2 protein encoded by a nucleic acid molecule that hybridizes with a nucleic acid sequence having SEQ ID NO:3, SEQ ID NO:6, SEQ ID NO:8, under conditions that allow less than or equal to about 10% base pair mismatch and an isolated COX-1 protein encoded by a nucleic acid molecule that hybridizes with a nucleic acid sequence having SEQ ID NO:1, SEQ ID NO:14, and/or SEQ ID NO:16, under conditions that allow less than or equal to about 10% base pair mismatch.

Another embodiment of the present invention includes a method to detect an inhibitor of canine COX-2 activity, said method comprising (a) contacting an isolated canine COX-2 protein of the present invention, with a putative inhibitory compound under conditions in which, in the absence of said compound, said protein has canine COX-2 protein activity, and (b) determining if said putative inhibitory compound inhibits canine COX-2 protein activity.

DETAILED DESCRIPTION OF THE INVENTION

The present invention provides for canine COX-1 and COX-2 nucleic acid molecules, proteins encoded by such nucleic acid molecules, antibodies raised against such proteins, and inhibitors of such proteins. As used herein, canine COX-2 nucleic acid molecules and proteins encoded by such nucleic acid molecules are also referred to as dog COX-2, or COX-2, nucleic acid molecules and proteins respectively and canine COX-1 nucleic acid molecules and proteins encoded by such nucleic acid molecules are also referred to as dog COX-1, or COX-1, nucleic acid molecules and proteins respectively. Canine COX-1 and COX-2 nucleic acid molecules and proteins of the present invention can be isolated from a canid or prepared recombinantly or synthetically. Canine COX-1 and COX-2 nucleic acid molecules of the present invention can be RNA or DNA, or modified forms thereof, and can be double-stranded or single-stranded; examples of nucleic acid molecules include, but are not limited to, complementary DNA (cDNA) molecules, genomic DNA molecules, synthetic DNA molecules, DNA molecules which are specific tags for messenger RNA, and corresponding mRNA molecules. As used herein, the phrases "canine COX-2 protein" and "dog COX-2 protein" refer to a protein encoded by a canine COX-2 nucleic acid molecule and "canine COX-1 protein" and "dog COX-1 protein" refer to a protein encoded by a canine COX-1 nucleic acid molecule.

Canine COX-2 nucleic acid molecules of known length isolated from a canid, such as *Canis familiaris* are denoted "nCfCX2$_\#$", for example nCfCX2$_{3509}$, wherein "#" refers to the number of nucleotides in that molecule, and canine COX-2 proteins of known length are denoted "PCfCX2$_\#$" (for example PCfCX2$_{604}$) wherein "#" refers to the number of amino acid residues in that molecule. Similarly, canine COX-1 nucleic acid molecules of known length isolated from a canid, such as *Canis familiaris* are denoted "nCfCX1$_\#$", for example nCfCX1$_{2693}$, wherein "#" refers to the number of nucleotides in that molecule, and canine COX-1 proteins of known length are denoted "PCfCX1$_\#$" (for example PCfCX1$_{633}$) wherein "#" refers to the number of amino acid residues in that molecule.

The present invention also provides for canine COX-1 and COX-2 DNA molecules that are specific tags for messenger RNA molecules. Such DNA molecules can correspond to an entire or partial sequence of a messenger RNA, and therefore, a DNA molecule corresponding to such a messenger RNA molecule (i.e. a cDNA molecule), can encode a full-length or partial-length protein. A nucleic acid molecule encoding a partial-length protein can be used directly as a probe or indirectly to generate primers to identify and/or isolate a cDNA nucleic acid molecule encoding a corresponding, or structurally related, full-length protein. Such a partial cDNA nucleic acid molecule can also be used in a similar manner to identify a genomic nucleic acid molecule, such as a nucleic acid molecule that contains the complete gene including regulatory regions, exons and introns. Methods for using partial canine COX-1 and COX-2 cDNA molecules and sequences to isolate full-length and corresponding cDNA molecules are described in the examples herein below.

The proteins and nucleic acid molecules of the present invention can be obtained from their natural source, or can be produced using, for example, recombinant nucleic acid technology or chemical synthesis. Also included in the present invention is the use of these proteins and nucleic acid molecules as well as antibodies and inhibitory compounds thereto as therapeutic compositions to treat pain, inflammation, cancer, fever and osteoarthritis as well as in other applications, such as those disclosed below.

One embodiment of the present invention is an isolated protein that includes a canine COX-1 or COX-2 protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated canine COX-1 and COX-2 proteins of the present invention can be full-length proteins or any homologue of such proteins. An isolated protein of the present invention, including a homologue, can be identified in a straight-forward manner by the protein's ability to elicit an immune response against a canine COX-1 or COX-2 protein or by the protein's ability to exhibit COX-1 or COX-2 activity. Examples of canine COX-1 and COX-2 homologue proteins include canine COX-1 and COX-2 proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a canine COX-1 or COX-2 protein, and/or of binding to an antibody directed against a canine COX-1 or COX-2 protein. That is, when the homologue is administered to an animal as an immunogen, using techniques known to those skilled in the art, the animal will produce an immune response against at least one epitope of a natural canine COX-1 or COX-2 protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids or at least about 50 amino acids in length.

In one embodiment of the present invention a canine COX-2 homologue protein has COX-2 activity, i.e. the homologue exhibits an activity similar to its natural counterpart. Examples of such activities are disclosed herein. Methods to detect and measure such activities are known to those skilled in the art.

In one embodiment of the present invention a canine COX-1 homologue protein has COX-1 activity, i.e. the homologue exhibits an activity similar to its natural counterpart. Examples of such activities are disclosed herein. Methods to detect and measure such activities are known to those skilled in the art.

Canine COX-1 and COX-2 homologue proteins can be the result of natural allelic variation or natural mutation. Canine COX-1 and COX-2 protein homologues of the present invention can also be produced using techniques known in the art including, but not limited to, direct modifications to the protein or modifications to the gene encoding the protein using, for example, classic or recombinant DNA techniques to effect random or targeted mutagenesis.

Canine COX-1 and COX-2 proteins of the present invention are encoded by canine COX-1 and COX-2 nucleic acid molecules, respectively. As used herein, canine COX-1 and COX-2 nucleic acid molecules include nucleic acid sequences related to natural canine COX-1 and COX-2 genes, and, preferably, to *Canis familaris* COX-1 and COX-2 genes. As used herein, canine COX-1 and COX-2 genes include all regions such as regulatory regions that control production of canine COX-1 and COX-2 proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons such as is often found for a canine gene. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a *C. famiaris* COX-2 gene that includes the nucleic acid sequence SEQ ID NO:1, SEQ ID NO:4 and/or SEQ ID NO:7. These nucleic acid sequences are further described herein. For example, nucleic acid sequence SEQ ID NO:4 represents the deduced sequence of the coding strand of a *C. familiaris* cDNA denoted herein as *C. familiaris* COX-2 nucleic acid molecule nCWfCX2$_{3509}$, the production of which is disclosed in the Examples. Nucleic acid molecule SEQ ID NO:4 comprises an apparently full-length coding region. The complement of SEQ ID NO:4 (represented herein by SEQ ID NO:6) refers to the nucleic acid sequence of the strand fully complementary to the strand having SEQ ID NO:4, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. It should be noted that since nucleic acid sequencing technology is not entirely error-free, SEQ ID NO:4 (as well as other nucleic acid and protein sequences presented herein) represents an apparent nucleic acid sequence of the nucleic acid molecule encoding a canine COX-2 protein of the present invention.

Translation of SEQ ID NO:4, the coding strand of nCfCX2$_{3509}$, as well as translation of SEQ ID NO:7, the coding strand of nCfCX2$_{1812}$, which represents the coding region of nCfCX2$_{3527}$, yields a protein of about 604 amino acids, denoted herein as PCfCX2$_{604}$, the amino acid sequence of which is presented in SEQ ID NO:5, assuming a first in-frame codon extending from nucleotide 53-55 of SEQ ID NO:4, or from nucleotide 1 to nucleotide 3 of SEQ ID NO:7, respectively.

One embodiment of the present invention is a *C. famiaris* COX-1 gene that includes the nucleic acid sequence SEQ ID NO:9, SEQ ID NO:12 and/or SEQ ID NO:15. These nucleic acid sequences are further described herein. For example, nucleic acid sequence SEQ ID NO:12 represents the deduced sequence of the coding strand of a *C. familiaris* cDNA denoted herein as *C. familiaris* COX-1 nucleic acid molecule nCfCX1$_{2693}$, the production of which is disclosed in the Examples. Nucleic acid molecule SEQ ID NO:12 comprises an apparently full-length coding region. The complement of SEQ ID NO:12 (represented herein by SEQ ID NO:14) refers to the nucleic acid sequence of the strand fully complementary to the strand having SEQ ID NO:12, which can easily be determined by those skilled in the art.

Translation of SEQ ID NO:12, the coding strand of nCfCX1$_{2693}$, as well as translation of SEQ ID NO:15, the coding strand of nCfCX1$_{1899}$, which represents the coding region of nCfCX1$_{2712}$, yields a protein of about 633 amino acids, denoted herein as PCfCX1$_{633}$, the amino acid sequence of which is presented in SEQ ID NO:13, assuming a first in-frame codon extending from nucleotide 31-33 of SEQ ID NO:12, or from nucleotide 1 to nucleotide 3 of SEQ ID NO:15, respectively.

In one embodiment, a gene or other nucleic acid molecule of the present invention can be an allelic variant that includes a similar but not identical sequence to SEQ ID NO:15 SEQ ID NO:3, SEQ ID NO:4, SEQ ID NO:6, SEQ ID NO:7, SEQ ID NO:8, SEQ ID NO:9, SEQ ID NO:11, SEQ ID NO:12, SEQ ID NO:14, SEQ ID NO:15, and/or SEQ ID NO:16 For example, an allelic variant of a *C. familiaris* COX gene including SEQ ID NO:1, SEQ ID NO:3, SEQ ID NO:4, SEQ ID NO:6, SEQ ID NO:7, SEQ ID NO:8, SEQ ID NO:9, SEQ ID NO:11, SEQ ID NO:12, SEQ ID NO:14, SEQ ID NO:15, and/or SEQ ID NO:16 is a gene that occurs at essentially the same locus (or loci) in the genome as the gene including SEQ ID NO:1, SEQ ID NO:3, SEQ ID NO:4, SEQ ID NO:6, SEQ ID NO:7, SEQ ID NO:8, SEQ ID NO:9, SEQ ID NO:11, SEQ ID NO:12, SEQ ID NO:14, SEQ ID NO:15, and/or SEQ ID NO: 16, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given canid, since the genome is diploid, and sexual reproduction will result in the reassortment of alleles.

In one embodiment of the present invention, isolated canine COX-1 and COX-2 proteins are encoded by nucleic acid molecules that hybridize under stringent hybridization conditions to genes or other nucleic acid molecules encoding canine COX-1 and COX-2 proteins, respectively. The minimal size of canine COX-1 and COX-2 proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the canine COX-1 or COX-2 nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a canine COX-1 or COX-2 protein is at least about 12 to about 15 nucleotides in length if the nucleic acid molecule is GC-rich and at least about 15 to about 17 bases in length if it is AT-rich. The minimal size of a nucleic acid molecule used to encode a canine COX-1 or COX-2 protein homologue of the present invention is from about 12 to about 18 nucleotides in length. Thus, the minimal size of canine COX-1 and COX-2 protein homologues of the present invention is from about 4 to about 6 amino acids in length. There is no limit, other than a practical limit, on the maximal size of a nucleic acid molecule encoding a canine COX-1 or COX-2 protein of the present invention because a nucleic acid molecule of the present invention can include a portion of a gene or cDNA or RNA, an entire gene or cDNA or RNA, or multiple genes or cDNA or RNA. The preferred size of a protein encoded by a nucleic acid molecule of the present invention depends on whether a full-length, fusion, multivalent, or functional portion of such a protein is desired.

Stringent hybridization conditions are determined based on defined physical properties of the COX gene or other COX nucleic acid molecule to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning. A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\% G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a canine COX-1 or COX-2 nucleic acid molecule of about 150 bp in length or greater, the following conditions could preferably be used. The average G+C content of canine DNA is about 53%, as calculated from known canine nucleic acid sequences. The unknown nucleic acid molecules would be attached to a support membrane, and the 150 bp probe would be labeled, e.g. with a radioactive tag. The hybridization reaction could be carried out in a solution comprising 2×SSC in the absence of nucleic acid helix destabilizing compounds, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC in the absence of nucleic acid helix destabilizing compounds, the $T_m$ of perfect hybrids would be about 86° C.:

$81.5°$ C.$+16.6$ log$(0.15M)+(0.41\times53)-(500/150)-$
$(0.61\times0)=86.22°$ C.

Thus, to achieve hybridization with nucleic acid molecules having about 30% base pair mismatch, hybridization washes would be carried out at a temperature of less than or equal to 56° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 56° C.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SeqLab® Wisconsin Package™ Version 10.0-UNIX sequence analysis software, available from Genetics Computer Group, Madison, Wis.; and DNAsis® sequence analysis software, version 2.0, available from Hitachi Software, San Bruno, Calif. Such software programs represent a collection of algorithms paired with a graphical user interface for using the algorithms. The DNAsis version 2.0 software and SeqLab Wisconsin Package Version 10.0-UNIX software, for example, employ a particular algorithm, the Needleman-Wunsch algorithm to perform pair-wise comparisons between two sequences to yield a percentage identity score, see Needleman, S. B. and Wunch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SeqLab Wisconsin Package Version 10.0-UNIX software (hereinafter "SeqLab"), using the Pair-wise Comparison/Gap function with the nwsgapdna.cmp scoring matrix, the gap creation penalty and the gap extension penalties set at default values, and the gap shift limits set at maximum (hereinafter referred to as "SeqLab default parameters"). An additional preferred method to determine percent identity among amino acid sequences and also among nucleic acid sequences includes using the Higgins-Sharp algorithm, available in the DNAsis version 2.0 software (hereinafter "DNAsis"), with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the SeqLab software, using the SeqLab default parameters.

One embodiment of the present invention includes a canine COX-2 protein. A preferred canine COX-2 protein includes a protein encoded by a nucleic acid molecule that hybridizes under conditions that preferably allow less than or equal to about 10% base pair mismatch, preferably under conditions that allow less than or equal to about 8% base pair mismatch, preferably under conditions that allow less than or equal to about 5% base pair mismatch or preferably under conditions that allow less than or equal to about 2% base pair mismatch with a nucleic acid molecule selected from the group consisting of SEQ ID NO:3, SEQ ID NO:6 and/or SEQ ID NO:8.

One embodiment of the present invention includes a canine COX-1 protein. A preferred canine COX-1 protein includes a protein encoded by a nucleic acid molecule that hybridizes under conditions that preferably allow less than or equal to about 10% base pair mismatch, preferably under conditions that allow less than or equal to about 8% base pair mismatch, preferably under conditions that allow less than or equal to about 5% base pair mismatch or preferably under conditions that allow less than or equal to about 2% base pair mismatch with a nucleic acid molecule selected from the group consisting of SEQ ID NO:11, SEQ ID NO:14 and/or SEQ ID NO:16.

Another embodiment of the present invention includes a canine COX-2 protein encoded by a nucleic acid molecule that hybridizes under conditions comprising, (a) hybridizing in a solution comprising 1×SSC in the absence of nucleic acid helix destabilizing compounds, at a temperature of about 37° C. and (b) washing in a solution comprising 1×SSC in the absence of nucleic acid helix destabilizing compounds, at a temperature of about 76° C., to an isolated nucleic acid molecule selected from the group consisting of SEQ ID NO:3, SEQ ID NO:6 and/or SEQ ID NO:8.

Another embodiment of the present invention includes a canine COX-1 protein encoded by a nucleic acid molecule that hybridizes under conditions comprising, (a) hybridizing in a solution comprising 1×SSC in the absence of nucleic acid helix destabilizing compounds, at a temperature of about 37° C. and (b) washing in a solution comprising 1×SSC in the absence of nucleic acid helix destabilizing compounds, at a temperature of about 76° C., to an isolated nucleic acid molecule selected from the group consisting of SEQ ID NO:11, SEQ ID NO:14 and/or SEQ ID NO:16.

Another preferred canine COX-2 protein of the present invention includes a protein that is encoded by a nucleic acid molecule that is preferably at least about 90% identical, preferably about at least 92% identical, preferably about at least 95% identical or preferably about at least 98% identical to a nucleic acid molecule having the nucleic acid sequence SEQ ID NO:1, SEQ ID NO:4 and/or SEQ ID NO:7; also preferred are fragments (i.e. portions) of such proteins encoded by nucleic acid molecules that are at least about 75 nucleotides. Percent identity as used herein is determined using the Needleman-Wunsch algorithm, available in the SeqLab software using default parameters.

Another preferred canine COX-1 protein of the present invention includes a protein that is encoded by a nucleic acid molecule that is preferably at least about 90% identical, preferably about at least 92% identical, preferably about at least 95% identical or preferably about at least 98% identical to a nucleic acid molecule having the nucleic acid sequence SEQ ID NO:9, SEQ ID NO:12 and/or SEQ ID NO:15; also preferred are fragments (i.e. portions) of such proteins encoded by nucleic acid molecules that are at least about 75 nucleotides. Percent identity as used herein is determined using the Needleman-Wunsch algorithm, available in the SeqLab software using default parameters.

Additional preferred canine COX-2 proteins of the present invention include proteins having the amino acid sequence SEQ ID NO:2 and/or SEQ ID NO:5, and proteins comprising homologues of a protein having the amino acid sequence SEQ ID NO:2 and/or SEQ ID NO:5, wherein such a homologue comprises at least one epitope that elicits an immune response against a protein having an amino acid sequence SEQ ID NO:2 and/or SEQ ID NO:5. Likewise, also preferred are proteins encoded by nucleic acid molecules comprising nucleic acid sequence SEQ ID NO:1, SEQ ID NO:4 and/or SEQ ID NO:7, or by homologues thereof.

Additional preferred canine COX-1 proteins of the present invention include proteins having the amino acid sequence SEQ ID NO:10 and/or SEQ ID NO:13, and proteins comprising homologues of a protein having the amino acid sequence SEQ ID NO:10 and/or SEQ ID NO:13, wherein such a homologue comprises at least one epitope that elicits an immune response against a protein having an amino acid sequence SEQ ID NO:10 and/or SEQ ID NO:13. Likewise, also preferred are proteins encoded by nucleic acid molecules comprising nucleic acid sequence SEQ ID NO:9, SEQ ID NO:12 and/or SEQ ID NO:15, or by homologues thereof.

A preferred isolated COX-2 protein of the present invention is a protein encoded by at least one of the following nucleic acid molecules: $nCfCX2_{542}$, $nCfCX2_{3509}$, and $nCfCX2_{1812}$, or allelic variants of any of these nucleic acid molecules. Also preferred is an isolated protein encoded by a nucleic acid molecule having nucleic acid sequence SEQ ID NO:1, SEQ ID NO:4, and/or SEQ ID NO:7; or a protein encoded by an allelic variant of any of these listed nucleic acid molecules.

A preferred isolated COX-1 protein of the present invention is a protein encoded by at least one of the following nucleic acid molecules: $nCfCX1_{275}$, $nCfCX1_{2693}$, and $nCFCX1_{1899}$, or allelic variants of any of these nucleic acid molecules. Also preferred is an isolated protein encoded by a nucleic acid molecule having nucleic acid sequence SEQ ID NO:9, SEQ ID NO:12 and/or SEQ ID NO:15; or a protein encoded by an allelic variant of any of these listed nucleic acid molecules.

Preferred proteins of the present invention include proteins that are at least about 95%, preferably about 98%, preferably about 99% or preferably about 100% identical to $PCfCX2_{180}$, and $PCfCX2_{604}$. Additionally preferred are proteins encoded by allelic variants of a nucleic acid molecules encoding proteins $PCfCX2_{180}$, and $PCfCX2_{604}$. Also preferred are fragments thereof having at least about 115 amino acid residues.

Preferred proteins of the present invention include proteins that are at least about 95%, preferably about 98%, preferably about 99% or preferably about 100% identical to $PCfCX1_{91}$, and $PCfCX1_{633}$. Additionally preferred are proteins encoded by allelic variants of a nucleic acid molecules encoding proteins $PCfCX1_{91}$, and $PCfCX1_{633}$. Also preferred are fragments thereof having at least about 75 amino acid residues.

Preferred canine COX-2 proteins of the present invention include proteins having amino acid sequences that are at least about 95%, preferably at least about 98%, preferably at least about 99%, or preferably about 100% identical to amino acid sequence SEQ ID NO:2 and/or SEQ ID NO:5; and proteins encoded by allelic variants of nucleic acid molecules encoding canine COX-2 proteins having amino acid sequences SEQ ID NO:2 and/or SEQ ID NO:5. Also preferred are fragments thereof having at least about 115 amino acid residues.

Preferred canine COX-1 proteins of the present invention include proteins having amino acid sequences that are at least about 95%, preferably at least about 98%, preferably at least about 99%, or preferably about 100% identical to amino acid sequence SEQ ID NO:10 and/or SEQ ID NO:13; and proteins encoded by allelic variants of nucleic acid molecules encoding canine COX-1 proteins having amino acid sequences SEQ ID NO:10 and/or SEQ ID NO:13. Also preferred are fragments thereof having at least about 75 amino acid residues.

In one embodiment of the present invention, *C. familiaris* COX-2 proteins comprise amino acid sequence SEQ ID NO:2 and/or SEQ ID NO:5 (including, but not limited to, the proteins consisting of amino acid sequence SEQ ID NO:2 and/or SEQ ID NO:5, fusion proteins and multivalent proteins), and proteins encoded by allelic variants of nucleic acid molecules encoding proteins having amino acid sequence SEQ ID NO:2 and/or SEQ ID NO:5.

In one embodiment of the present invention, *C. familiaris* COX-1 proteins comprise amino acid sequence SEQ ID NO:10 and/or SEQ ID NO:13 (including, but not limited to, the proteins consisting of amino acid sequence SEQ ID NO:10 and/or SEQ ID NO:13, fusion proteins and multivalent proteins), and proteins encoded by allelic variants of nucleic acid molecules encoding proteins having amino acid sequence SEQ ID NO:10 and/or SEQ ID NO:13.

In one embodiment, a preferred canine COX-2 protein comprises an amino acid sequence of at least about 35 amino acids, preferably at least about 50 amino acids, preferably at least about 100 amino acids, preferably at least about 125 amino acids, preferably at least about 150 amino acids, preferably at least about 175 amino acids, preferably at least about 200 amino acids, preferably at least about 250 amino acids, preferably at least about 300 amino acids, preferably at least about 350 amino acids, preferably at least about 400 amino acids, preferably at least about 450 amino acids, preferably at least about 500 amino acids, even preferably at least about 550 amino acids, or preferably at least about 600 amino acids. In another embodiment, preferred canine COX-2 proteins comprise full-length proteins, i.e., proteins encoded by full-length coding regions, or post-translationally modified proteins thereof, such as mature proteins from which initiating methionine and/or signal sequences or "pro" sequences have been removed.

In one embodiment, a preferred canine COX-1 protein comprises an amino acid sequence of at least about 35 amino acids, preferably at least about 50 amino acids, preferably at least about 60 amino acids, preferably at least about 70 amino acids, preferably at least about 80 amino acids, preferably at least about 90 amino acids, preferably at least about 100 amino acids, preferably at least about 125 amino acids, preferably at least about 150 amino acids, preferably at least about 175 amino acids, preferably at least about 200 amino acids, preferably at least about 250 amino acids, preferably at least about 300 amino acids, preferably at least about 350 amino acids, preferably at least about 400 amino acids, preferably at least about 450 amino acids, preferably at least about 500 amino acids, preferably at least about 550 amino acids, preferably at least about 600 amino acids, or preferably at least about 630 amino acids. In another embodiment, preferred canine COX-1 proteins comprise full-length proteins, i.e., proteins encoded by full-length coding regions, or post-translationally modified proteins thereof, such as mature proteins from which initiating methionine and/or signal sequences or "pro" sequences have been removed.

A fragment of a canine COX-2 protein of the present invention preferably comprises at least about 115 amino acids, preferably at least about 120 amino acids, preferably at least about 130 amino acids, preferably at least about 140 amino acids, preferably at least about 150 amino acids, preferably at least about 160 amino acids, preferably at least about 170 amino acids, or preferably at least about 180 amino acids in length.

A fragment of a canine COX-1 protein of the present invention preferably comprises at least about 75 amino acids, preferably at least about 80 amino acids, preferably at least about 85 amino acids, preferably at least about 90 amino acids, preferably at least about 95 amino acids, or preferably at least about 100 amino acids in length.

Additional preferred canine COX-2 proteins of the present invention include proteins encoded by nucleic acid molecules comprising at least a portion of $nCfCX2_{542}$, $nCfCX2_{3509}$, and/or $nCfCX2_{1812}$, as well as canine COX-2 proteins encoded by allelic variants of such nucleic acid molecules. A portion of such canine COX-2 nucleic acid molecule is preferably at least 75 nucleotides in length.

Additional preferred canine COX-1 proteins of the present invention include proteins encoded by nucleic acid molecules comprising at least a portion of $nCfCX1_{275}$, $nCfCX1_{2693}$, and/or $nCFCX1_{1899}$, as well as canine COX-1 proteins encoded by allelic variants of such nucleic acid molecules. A portion of such canine COX-1 nucleic acid molecule is preferably at least 75 nucleotides in length.

Also preferred are canine COX-2 proteins encoded by nucleic acid molecules having nucleic acid sequences comprising at least a portion of SEQ ID NO:1, SEQ ID NO:4, and/or SEQ ID NO:7, as well as allelic variants of these nucleic acid molecules. A portion of such canine COX-2 nucleic acid molecule is preferably at least 75 nucleotides in length.

Also preferred are canine COX-1 proteins encoded by nucleic acid molecules having nucleic acid sequences comprising at least a portion of SEQ ID NO:9, SEQ ID NO:12, and/or SEQ ID NO; 15, as well as allelic variants of these nucleic acid molecules. A portion of such canine COX-1 nucleic acid molecule is preferably at least 75 nucleotides in length.

In another embodiment, a preferred canine COX-2 protein of the present invention is encoded by a nucleic acid molecule comprising at least about 75 nucleotides, preferably at least about 80 nucleotides, preferably at least about 85 nucleotides, preferably at least about 90 nucleotides, preferably at least about 95 nucleotides, preferably at least about 100 nucleotides, preferably at least about 150 nucleotides, preferably at least about 350 nucleotides, preferably at least about 450 nucleotides, preferably at least about 550 nucleotides, preferably at least about 650 nucleotides, preferably at least about 750 nucleotides, preferably at least about 1000 nucleotides, preferably at least about 1500 nucleotides, preferably at least about 1750 nucleotides, preferably at least about 2000 nucleotides, preferably at least about 2250 nucleotides, preferably at least about 2500 nucleotides, preferably at least about 2750 nucleotides preferably at least about 3000 nucleotides, preferably at least about 3250 nucleotides or preferably at least about 3500 nucleotides in length. Within this embodiment is a canine COX-2 protein encoded by at least a portion of $nCfCX2_{3509}$, or by an allelic variant of any of these nucleic acid molecules. Preferred canine COX-2 proteins of the present invention are encoded by nucleic acid molecules comprising apparently full-length canine COX-2 coding region, i.e., nucleic acid molecules encoding an apparently full-length canine COX-2 protein.

In another embodiment, a preferred canine COX-1 protein of the present invention is encoded by a nucleic acid molecule comprising at least about 75 nucleotides, preferably at least about 80 nucleotides, preferably at least about 85 nucleotides, preferably at least about 90 nucleotides, preferably at least about 95 nucleotides, preferably at least about 100 nucleotides, preferably at least about 150 nucleotides, preferably at least about 350 nucleotides, preferably at least about 450 nucleotides, preferably at least about 550 nucleotides, preferably at least about 650 nucleotides, preferably at least about 750 nucleotides, preferably at least about 1000 nucleotides, preferably at least about 1500 nucleotides, preferably at least about 1750 nucleotides preferably at least about 2000 nucleotides, preferably at least about 2250 nucleotides, preferably at least about 2500 nucleotides, or preferably at least about 2700 nucleotides in length. Within this embodiment is a canine COX-1 protein encoded by at least a portion of $nCfCX1_{2693}$, or by an allelic variant of any of these nucleic acid molecules. Preferred canine COX-1 proteins of the present invention are encoded by nucleic acid molecules comprising apparently full-length canine COX-1 coding region, i.e., nucleic acid molecules encoding an apparently full-length canine COX-1 protein.

Preferred canine COX-1 and COX-2 proteins of the present invention can be used to develop inhibitors that, when administered to an animal in an effective manner, are capable of treating pain, inflammation, cancer, fever, osteoarthritis and other diseases as described herein. In accordance with the present invention, the ability of an inhibitor of the present invention to treat an animal refers to the ability of that protein to, for example, treat, ameliorate and/or prevent pain, inflammation, cancer, fever, osteoarthritis and other diseases as described herein.

One embodiment of a canine COX-1 or COX-2 protein of the present invention is a fusion protein that includes a canine COX-1 or COX-2 protein-containing domain attached to one or more fusion segments. Suitable fusion segments for use with the present invention include, but are not limited to, segments that can: enhance a protein's stability; act as an immunopotentiator; and/or assist in purification of a canine COX-1 or COX-2 protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the canine COX-1 or COX-2-containing domain of the protein and can be susceptible to cleavage in order to enable straight-forward recovery of a canine COX-1 or COX-2 protein. Fusion proteins are preferably produced by culturing a recombinant cell transformed with a fusion nucleic acid molecule that encodes a protein including the fusion segment attached to either the carboxyl and/or amino terminal end of a canine COX-1 or COX-2-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of canine COX-1 or COX-2 proteins of the present invention. As used herein, a mimetope of a canine COX-1 or COX-2 protein of the present invention refers to any compound that is able to mimic the activity of such a canine COX-1 or COX-2 protein, often because the mimetope has a structure that mimics the particular canine COX-1 or COX-2 protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a canine COX-1 or COX-2 nucleic acid molecule, i.e. a nucleic acid molecule that can be isolated from a canine cDNA library. As used herein, canine COX-2 nucleic acid molecules has the same meaning as canine COX-2 nucleic acid molecule and canine COX-1 nucleic acid molecules has the same meaning as canine COX-1 nucleic acid molecule. The identifying characteristics of such nucleic acid molecules are heretofore described. A nucleic acid molecule of the present invention can include an isolated natural canine COX-1 or COX-2 gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a canine COX-1 or COX-2 nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated canine COX-1 or COX-2 nucleic acid molecules of the present invention, or homologues thereof, can be isolated from a natural source or produced using recombinant DNA technology (e.g., polymerase chain reaction (PCR) amplification or cloning) or chemical synthesis. Isolated canine COX-1 or COX-2 nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a canine COX-1 or COX-2 protein of the present invention.

A canine COX-1 or COX-2 nucleic acid molecule homologue can be produced using a number of methods known to those skilled in the art, see, for example, Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with canine COX-1 or COX-2 nucleic acid molecules or by screening the function of a protein encoded by the nucleic acid molecule (e.g., ability to elicit an immune response against at least one epitope of a canine COX-1 or COX-2 protein or to effect canine COX-1 or COX-2 activity).

An isolated canine COX-1 or COX-2 nucleic acid molecule of the present invention can include a nucleic acid sequence that encodes at least one canine COX-1 or COX-2 protein of the present invention respectively, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a canine COX-1 or COX-2 protein.

As will be disclosed in more detail below, a nucleic acid molecule of the present invention can be, or encode, an antisense RNA, a molecule capable of triple helix formation, a ribozyme, or other nucleic acid-based drug compound. In additional embodiments, a nucleic acid molecule of the present invention can encode a protective protein (e.g., a canine COX-1 or COX-2 protein of the present invention), the nucleic acid molecule being delivered to the animal, for example, by direct injection (i.e, as a genetic vaccine) or in a vehicle such as a recombinant virus vaccine or a recombinant cell vaccine.

In one embodiment of the present invention, a preferred canine COX-2 nucleic acid molecule includes an isolated nucleic acid molecule that hybridizes under conditions that preferably allow less than or equal to about 10% base pair mismatch, preferably under conditions that allow less than or equal to about 5% base pair mismatch or preferably under conditions that allow less than or equal to about 2% base pair mismatch with a nucleic acid molecule selected from the group consisting of SEQ ID NO:1, SEQ ID NO:3, SEQ ID NO:4, SEQ ID NO:6, SEQ ID NO:7, and/or SEQ ID NO:8.

In one embodiment of the present invention, a preferred canine COX-1 nucleic acid molecule includes an isolated nucleic acid molecule that hybridizes under conditions that preferably allow less than or equal to about 10% base pair mismatch, preferably under conditions that allow less than or equal to about 5% base pair mismatch or preferably under conditions that allow less than or equal to about 2% base pair mismatch with a nucleic acid molecule selected from the group consisting of SEQ ID NO:9, SEQ ID NO:11, SEQ ID NO:12, SEQ ID NO:14, SEQ ID NO:15, and/or SEQ ID NO:16.

Another embodiment of the present invention includes a canine COX-2 nucleic acid molecule, wherein said nucleic acid molecule hybridizes under conditions comprising, (a) hybridizing in solution comprising 1×SSC in the absence of nucleic acid helix destabilizing compounds, at a temperature of about 37° C. and (b) washing in a solution comprising 1×SSC in the absence of nucleic acid helix destabilizing compounds, at a temperature of about 76° C., to an isolated nucleic acid molecule selected from the group consisting of SEQ ID NO:1, SEQ ID NO:3, SEQ ID NO:4, SEQ ID NO:6, SEQ ID NO:7, and/or SEQ ID NO:8. Additional preferred nucleic acid molecules of the present invention include oligonucleotides of an isolated nucleic acid molecule, wherein said nucleic acid molecule hybridizes under conditions comprising, (a) hybridizing in solution comprising 1×SSC in the absence of nucleic acid helix destabilizing compounds, at a temperature of about 37° C. and (b) washing in a solution comprising 1×SSC in the absence of nucleic acid helix destabilizing compounds, at a temperature of about 76° C., to an isolated nucleic acid molecule selected from the group consisting of SEQ ID NO:1, SEQ ID NO:3, SEQ ID NO:4, SEQ ID NO:6, SEQ ID NO:7, and/or SEQ ID NO:8, wherein said oligonucleotide comprises at least about 18 nucleotides.

Another embodiment of the present invention includes a canine COX-1 nucleic acid molecule, wherein said nucleic acid molecule hybridizes under conditions comprising, (a) hybridizing in solution comprising 1×SSC in the absence of nucleic acid helix destabilizing compounds, at a temperature of about 37° C. and (b) washing in a solution comprising 1×SSC in the absence of nucleic acid helix destabilizing compounds, at a temperature of about 76° C., to an isolated nucleic acid molecule selected from the group consisting of SEQ ID NO:9, SEQ ID NO:11, SEQ ID NO:12, SEQ ID NO:14, SEQ ID NO:15, and/or SEQ ID NO:16. Additional preferred nucleic acid molecules of the present invention include oligonucleotides of an isolated nucleic acid molecule, wherein said nucleic acid molecule hybridizes under conditions comprising, (a) hybridizing in solution comprising 1×SSC in the absence of nucleic acid helix destabilizing compounds, at a temperature of about 37° C. and (b) washing in a solution comprising 1×SSC in the absence of nucleic acid helix destabilizing compounds, at a temperature of about 76° C., to an isolated nucleic acid molecule selected from the group consisting of SEQ ID NO:9, SEQ ID NO:11, SEQ ID NO:12, SEQ ID NO:14, SEQ ID NO:15, and/or SEQ ID NO:16, wherein said oligonucleotide comprises at least about 18 nucleotides.

Additional preferred canine COX-2 nucleic acid molecules of the present invention include nucleic acid molecules comprising a nucleic acid sequence that is preferably at least about 90%, preferably at least about 95%, or preferably at least about 98% identical to a nucleic acid sequence selected from the group consisting of SEQ ID NO:1, SEQ ID NO:3, SEQ ID NO:4, SEQ ID NO:6, SEQ ID NO:7, and/or SEQ ID NO:8. Also preferred are oligonucleotides of any of such nucleic acid molecules. Percent identity as used herein is determined using the Needleman-Wunsch algorithm, available in the SeqLab software using default parameters.

Additional preferred canine COX-1 nucleic acid molecules of the present invention include nucleic acid molecules comprising a nucleic acid sequence that is preferably at least about 90%, preferably at least about 95%, or preferably at least about 98% identical to a nucleic acid sequence selected from the group consisting of SEQ ID NO:9, SEQ ID NO:11, SEQ ID NO:12, SEQ ID NO:14, SEQ ID NO:15, and/or SEQ ID NO:16. Also preferred are oligonucleotides of any of such nucleic acid molecules. Percent identity as used herein is determined using the Needleman-Wunsch algorithm, available in the SeqLab software using default parameters.

One embodiment of the present invention is a nucleic acid molecule comprising all or part of nucleic acid molecules $nCfCX2_{542}$, $nCfCX2_{3509}$, and/or $nCfCX2_{1812}$, or allelic variants of these nucleic acid molecules. Another preferred nucleic acid molecule of the present invention includes at least a portion of nucleic acid sequence SEQ ID NO:1, SEQ ID NO:3, SEQ ID NO:4, SEQ ID NO:6, SEQ ID NO:7, and/or SEQ ID NO:8, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:1, SEQ ID NO:3, SEQ ID NO:4, SEQ ID NO:6, SEQ ID NO:7, and/or SEQ ID NO:8. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

One embodiment of the present invention is a nucleic acid molecule comprising all or part of nucleic acid molecules $nCfCX1_{275}$, $nCfCX1_{2693}$, and/or $nCfCX1_{1899}$, or allelic variants of these nucleic acid molecules. Another preferred nucleic acid molecule of the present invention includes at least a portion of nucleic acid sequence SEQ ID NO:9, SEQ ID NO:11, SEQ ID NO:12, SEQ ID NO:14, SEQ ID NO:15, and/or SEQ ID NO:16, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:9, SEQ ID NO:11, SEQ ID NO:12, SEQ ID NO:14, SEQ ID NO:15, and/or SEQ ID NO:16. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, canine COX-2 nucleic acid molecule of the present invention encodes a protein that is at least about 90%, preferably at least about 95%, preferably at least about 98%, preferably at least about 99%, or preferably at least about 100% identical to $PCfCX2_{180}$, and $PCfCX2_{604}$.

In one embodiment, canine COX-1 nucleic acid molecule of the present invention encodes a protein that is at least about 90%, preferably at least about 95%, preferably at least about 98%, preferably at least about 99%, or preferably at least about 100% identical to $PCfCX1_{91}$, and $PCfCX1_{633}$.

In one embodiment, a canine COX-2 nucleic acid molecule of the present invention encodes a protein having an amino acid sequence that is at least about 95%, preferably at least about 98%, preferably at least about 99%, or preferably at least about 100% identical to SEQ ID NO:2 and/or SEQ ID NO:5. The present invention also includes a canine COX-2 nucleic acid molecule encoding a protein having at least a portion of SEQ ID NO:2 and/or SEQ ID NO:5, as well as allelic variants of a nucleic acid molecule encoding a protein having these sequences, including nucleic acid molecules that have been modified to accommodate codon usage properties of the cells in which such nucleic acid molecules are to be expressed.

In one embodiment, a canine COX-1 nucleic acid molecule of the present invention encodes a protein having an amino acid sequence that is at least about 95%, preferably at least about 98%, preferably at least about 99%, or preferably at least about 100% identical to SEQ ID NO:10 and/or SEQ ID NO:13. The present invention also includes a canine COX-1 nucleic acid molecule encoding a protein having at least a portion of SEQ ID NO:10 and/or SEQ ID NO:13, as well as allelic variants of a nucleic acid molecule encoding a protein having these sequences, including nucleic acid molecules that have been modified to accommodate codon usage properties of the cells in which such nucleic acid molecules are to be expressed.

In another embodiment, a preferred canine COX-2 nucleic acid molecule of the present invention comprises a nucleic acid molecule comprising at least about 75 nucleotides, preferably at least about 100 nucleotides, preferably at least about 150 nucleotides, preferably at least about 350 nucleotides, preferably at least about 450 nucleotides, preferably at least about 550 nucleotides, preferably at least about 650 nucleotides, preferably at least about 750 nucleotides, preferably at least about 1000 nucleotides, preferably at least about 1500 nucleotides, preferably at least about 1750 nucleotides preferably at least about 2000 nucleotides, preferably at least about 2250 nucleotides, preferably at least about 2500 nucleotides, preferably at least about 2750 nucleotides preferably at least about 3000 nucleotides, preferably at least about 3250 nucleotides or preferably at least about 3500 nucleotides in length.

In another embodiment, a preferred canine COX-1 nucleic acid molecule of the present invention comprises a nucleic acid molecule comprising at least about 75 nucleotides, preferably at least about 100 nucleotides, preferably at least about 150 nucleotides, preferably at least about 350 nucleotides, preferably at least about 450 nucleotides, preferably at least about 550 nucleotides, preferably at least about 650 nucleotides, preferably at least about 750 nucleotides, preferably at least about 1000 nucleotides, preferably at least about 1500 nucleotides, preferably at least about 1750 nucleotides preferably at least about 2000 nucleotides, preferably at least about 2250 nucleotides, preferably at least about 2500 nucleotides, or preferably at least about 2700 nucleotides in length.

In another embodiment, a preferred canine COX-2 nucleic acid molecule encodes a protein comprising at least about 115 amino acids, preferably at least about 125 amino acids, preferably at least about 150 amino acids, preferably at least about 200 amino acids, preferably at least about 300 amino acids, preferably at least about 400 amino acids, preferably at least about 500 amino acids, preferably at least about 550 amino acids, or preferably at least about 600 amino acids.

In another embodiment, a preferred canine COX-1 nucleic acid molecule encodes a protein comprising at least about 75 amino acids, preferably at least about 100 amino acids, preferably at least about 150 amino acids, preferably at least about 200 amino acids, preferably at least about 300 amino acids, preferably at least about 400 amino acids, preferably at least about 500 amino acids, preferably at least about 550 amino acids, preferably at least about 600 amino acids, or preferably at least about 635 amino acids.

In another embodiment, a preferred canine COX-1 or COX-2 nucleic acid molecule of the present invention comprises an apparently full-length canine COX-1 or COX-2 coding region, i.e., the preferred nucleic acid molecule encodes an apparently full-length canine COX-1 or COX-2 protein, respectively, or a post-translationally modified protein thereof. In one embodiment, a preferred canine COX-1 or COX-2 nucleic acid molecule of the present invention encodes a mature protein.

In another embodiment, a preferred canine COX-2 nucleic acid molecule of the present invention comprises a nucleic acid molecule comprising SEQ ID NO; 1, SEQ ID NO:3, SEQ ID NO:4, SEQ ID NO:6, SEQ ID NO:7, and/or SEQ ID NO:8, or a fragment thereof and a preferred canine COX-1 nucleic acid molecule of the present invention comprises a nucleic acid molecule comprising SEQ ID NO:9, SEQ ID NO:11, SEQ ID NO:12, SEQ ID NO:14, SEQ ID NO:15, and/or SEQ ID NO:16, or a fragment thereof.

A fragment of a canine COX-2 nucleic acid molecule of the present invention preferably comprises at least about 75 nucleotides, preferably at least about 80 nucleotides, preferably at least about 90 nucleotides, or preferably at least about 100 contiguous nucleotides identical in sequence to a corresponding contiguous sequence selected from the group consisting of SEQ ID NO:1, SEQ ID NO:3, SEQ ID NO:4, SEQ ID NO:6, SEQ ID NO:7, and/or SEQ ID NO:8.

A fragment of a canine COX-1 nucleic acid molecule of the present invention preferably comprises at least about 75 nucleotides, preferably at least about 80 nucleotides, preferably at least about 90 nucleotides, or preferably at least about 100 contiguous nucleotides identical in sequence to a corresponding contiguous sequence selected from the group consisting of SEQ ID NO:9, SEQ ID NO:11, SEQ ID NO:12, SEQ ID NO:14, SEQ ID NO:15, and/or SEQ ID NO:16.

The phrase, a nucleic acid molecule comprising at least "x" contiguous, or consecutive nucleotides identical in sequence to at least "x" contiguous, or consecutive nucleotides of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to a molecule of the present invention, as well as extensions that show similarity or identity to cited nucleic acids sequences or portions thereof.

Knowing the nucleic acid sequences of certain canine COX-1 and COX-2 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other canine COX-2 nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include cDNA libraries as well as genomic DNA libraries. Similarly, preferred DNA sources to screen or from which to amplify nucleic acid molecules include cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising *C. familiaris* COX-1 or COX-2 nucleic acid molecules or other canine COX-1 or COX-2 nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 100 to 200 nucleotides. The present invention includes oligonucleotides that can be used as, for example, probes to identify nucleic acid molecules, primers to produce nucleic acid molecules, or therapeutic reagents to inhibit canine COX-1 or COX-2 protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of canine COX-1 or COX-2 nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with canids, such as *C. familiaris* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCfCX2_{542}$, $nCfCX2_{3509}$, $nCfCX2_{1812}$, $nCfCX1_{275}$, $nCfCX1_{2693}$, and/or $nCFCX1_{1899}$.

Recombinant molecules of the present invention may also (a) contain secretory signals (i.e., signal segment nucleic acid sequences) to enable an expressed canine COX-1 or COX-2 protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include C canine COX-1 or COX-2 nucleic acid molecules disclosed herein. Preferred nucleic acid molecules with which to transform a cell include $nCfCX2_{542}$, $nCfCX2_{3509}$, $nCfCX2_{812}$, $nCfCX1_{275}$, $nCfCX1_{2693}$, and/or $nCFCX1_{1899}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing canine COX-1 or COX-2 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include *Salmonella, Escherichia, Bacillus, Caulobacter, Listeria, Saccharomyces, Pichia, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 x3987 and SR-11 x4072; *Caulobacter; Pichia; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including canine COX-1 or COX-2 nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated canine COX-1 and/or COX-2 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a canine COX-1 and/or COX-2 protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a canine COX-2 protein of the present invention or a mimetope thereof (e.g., anti-canine COX-2 antibodies) and isolated antibodies that selectively bind to a canine COX-1 protein of the present invention or a mimetope thereof. As used herein, the term "selectively binds to" a protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-canine COX-1 or COX-2 antibody of the present invention preferably selectively binds to a canine COX-1 or COX-2 protein, respectively, in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce canine COX-1 and/or COX-2 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to treat the animal for a condition susceptible to treatment by such antibodies and/or (b) as tools to screen expression libraries and/or to recover desired proteins of the present invention from a mixture of proteins and other contaminants.

One embodiment of the present invention is a therapeutic composition that, when administered to an animal, is capable of treating that animal for diseases or conditions described herein, such as pain, inflammation, cancer, fever, and osteoarthritis. Therapeutic compositions of the present invention include at least one of the following protective molecules: an isolated canine COX-2 protein; an isolated canine COX-1 protein; a mimetope of an isolated canine COX-2 protein; a mimetope of an isolated canine COX-1 protein; an isolated canine COX-2 nucleic acid molecule; an isolated canine COX-1 nucleic acid molecule; an isolated anti-canine COX-2 antibody; an isolated anti-canine COX-1 antibody; and/or a compound derived from said isolated canine COX-2 protein that inhibits canine COX-2 protein activity. A therapeutic composition of the present invention can further comprise a component selected from the group of an excipient, a carrier, and/or an adjuvant; these components are described further herein. As used herein, a therapeutic molecule or therapeutic compound refers to a compound that, when administered to an animal in an effective manner, is able to treat, ameliorate, and/or prevent a given disease or condition. One example of a protective molecule is a vaccine, such as, but not limited to, a naked nucleic acid vaccine, a recombinant virus vaccine, a recombinant cell vaccine, and a recombinant protein vaccine. Another example of a protective molecule is a compound that inhibits canine COX-2 protein activity, such as an isolated antibody that selectively binds to a canine COX-2 protein, a substrate analog of a canine COX-2 protein, anti-sense-, triplex formation-, ribozyme-, and/or RNA drug-based compounds, or other inorganic or organic molecules that inhibit canine COX-2 protein activity. Inhibiting canine COX-2 protein activity can refer to the ability of a compound to reduce the activity of, e.g. the specific activity, canine COX-2 proteins. Inhibiting canine COX-2 protein activity can also refer to the ability of a compound to reduce the amount of canine COX-2 protein in an animal. Preferred is a compound that is COX-2 specific, i.e. a compound that does not substantially inhibit COX-1 activity.

Another embodiment of the present invention includes a method to treat a condition in an animal. Such a method includes the step of administering to the animal a therapeutic composition comprising a therapeutic compound selected from the group consisting of (a) an isolated canine COX-2 protein; (b) a mimetope of an isolated canine COX-2 protein; (c) an isolated canine COX-2 nucleic acid molecule; (d) an isolated anti-canine COX-2 antibody and (e) a compound that inhibits canine COX-2 protein activity.

As used herein, the term derived, or the term derived from, refers to a peptide, antibody, mimetope, nucleic acid molecule, or other compound that was obtained from a canine COX-1 or COX-2 protein or nucleic acid molecule of the present invention. Methods to obtain derivatives from a canine COX-1 and/or COX-2 molecule of the present invention are known in the art, and as such include, but are not limited to molecular modeling of canine COX-1 and/or COX-2 proteins to determine active sites, and predicting from these active sites smaller fragments and/or mimetopes that retain and/or mimic these active sites, thereby inhibiting canine COX-2 protein activity. Other inhibitors of COX-2 activity can also be obtained in a variety of ways, including but not limited to screening of peptide or small chemical compound libraries against canine COX-2 proteins of the present invention; and screening of polyclonal or monoclonal antibodies to find antibodies that specifically bind canine COX-2 proteins of the present invention.

A canine COX-2 protein inhibitor of the present invention (i.e. an inhibitor of a COX-2 protein) is identified by its ability to mimic, bind to, modify, or otherwise interact with, a canine COX-2 protein, thereby inhibiting the activity of a natural canine COX-2 protein. Suitable inhibitors of canine COX-2 protein activity are compounds that inhibit canine COX-2 protein activity in at least one of a variety of ways: (a) by binding to or otherwise interacting with or otherwise modifying canine COX-2 protein sites; (b) by binding to or otherwise interacting with or otherwise modifying the canine COX-2 protein active site; (c) by binding to the canine COX-2 protein and thus reducing the availability of the canine COX-2 protein in solution; (d) by mimicking a COX-2 protein; and (e) by interacting with other regions of the canine COX-2 protein to inhibit canine COX-2 protein activity, for example, by allosteric interaction.

Canine COX-2 protein inhibitors can be used directly as compounds in compositions of the present invention to treat animals as long as such compounds are not harmful to host animals being treated. Preferred canine COX-2 protein inhibitors of the present invention include, but are not limited to, canine COX-2 protein substrate analogs, and other molecules that bind to a canine COX-2 protein (e.g., to an allosteric site) in such a manner that the activity of the canine COX-2 protein is inhibited. A canine COX-2 protein substrate analog refers to a compound that interacts with (e.g., binds to, associates with, modifies) the active site of a canine COX-2 protein. A preferred canine COX-2 protein substrate analog inhibits canine COX-2 protein activity. Canine COX-2 protein substrate analogs can be of any inorganic or organic composition. Canine COX-2 protein substrate analogs can be, but need not be, structurally similar to a canine COX-2 protein natural substrate as long as they can interact with the active site of that canine COX-2 protein. Canine COX-2 protein substrate analogs can be designed using computer-generated structures of canine COX-2 proteins of the present invention or computer structures of canine COX-2 protein's natural substrates. Preferred sites to model include one or more of the active sites of canine COX-2 proteins. Substrate analogs can also be obtained by generating random samples of molecules, such as oligonucleotides, peptides, peptidomimetic compounds, or other inorganic or organic molecules, and screening such samples for their ability to interfere with interaction between canine COX-2 proteins and their substrates, e.g. by affinity chromatography techniques. A preferred canine COX-2 protein substrate analog is a canine COX-2 protein mimetic compound, i.e., a compound that is structurally and/or functionally similar to a natural substrate of a canine COX-2 protein of the present invention, particularly to the region of the substrate that interacts with the canine COX-2 protein active site, but that inhibits canine COX-2 protein activity upon interacting with the canine COX-2 protein active site.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, serum albumin, preservatives, etc., to which sterile water or saline can be added prior to administration.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition. The therapeutic composition is preferably released over a period of time ranging from about 4 to about 48 hours. A controlled release formulation of the present invention is capable of effecting a treatment preferably for at least about 4 hours, preferably for at least about 8 hours, preferably for at least about 12 hours, preferably for at least about 24 hours, preferably for at least about 36 hours, or preferably for at least about 48 hours.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of treating an animal when administered one or more times over a suitable time period. For example, a preferred single dose of an inhibitor is from about 1 microgram (μg) to about 50 milligrams (mg) of the therapeutic composition per kilogram body weight of the animal. Modes of administration can include, but are not limited to, subcutaneous, intradermal, intravenous, intranasal, oral, transdermal, intraocular, intranasal, conjunctival, and intramuscular routes. Methods of administration for other therapeutic compounds can be determined by one skilled in the art, and may include administration of a therapeutic composition one or more times. A preferred route of administration of an inhibitory compound is an oral formulation that, when fed to an animal, would enter the bloodstream of the animal to effect a treatment.

As discussed herein, one therapeutic composition of the present invention includes an inhibitor of canine COX-2 protein activity, i.e., a compound capable of substantially interfering with the function of a canine COX-2 protein. An inhibitor of canine COX-2 protein activity, or function, can be identified using canine COX-2 proteins of the present invention. A preferred inhibitor of canine COX-2 protein function is a compound capable of substantially interfering with the function of a canine COX-2 protein and which does not substantially interfere with the function of canine COX-1 proteins. As used herein, a compound that does not substantially inhibit or interfere with canine COX-1 proteins is one that, when administered to a host animal, the host animal shows no significant adverse effects attributable to the inhibition of COX-1 and which, when administered to an animal in an effective manner, is capable of treating that animal for a condition described herein (e.g. pain, inflammation, cancer, fever, osteoarthritis).

One embodiment of the present invention is a method to identify a compound capable of inhibiting canine COX-2 protein activity. Such a method includes the steps of (a) contacting (e.g., combining, mixing) an isolated canine COX-2 protein of the present invention, with a putative inhibitory compound under conditions in which, in the absence of the compound, the protein has canine COX-2 protein activity, and (b) determining if the putative inhibitory compound inhibits the activity. Canine COX-2 protein activity can be determined in a variety of ways known in the art, including but not limited to determining the ability of canine COX-2 protein to bind to or otherwise interact with a substrate. Such conditions under which a canine COX-2 protein has canine COX-2 protein activity include conditions in which a canine COX-2 protein has a correct three-dimensionally folded structure under physiologic conditions, i.e. physiologic pH, physiologic ionic concentrations, and physiologic temperatures.

Putative inhibitory compounds to screen include antibodies (including fragments and mimetopes thereof), putative substrate analogs, and other, preferably small, organic or inorganic molecules. Methods to determine canine COX-1 and COX-2 protein activity are known to those skilled in the art and examples are disclosed herein.

A preferred method to identify a compound capable of inhibiting canine COX-2 protein activity includes contacting an isolated canine COX-2 protein having an amino acid sequence selected from the group consisting of: (a) a protein comprising an amino acid sequence selected from the group consisting of SEQ ID NO:2 and SEQ ID NO:5; and (b) a protein comprising an at least 115 consecutive amino acid portion identical in sequence to an at least 115 consecutive amino acid portion of a sequence as set forth in (a), wherein the protein has canine COX-2 protein activity; (c) a protein comprising a fragment of a protein as set forth in (a), wherein the fragment has an activity selected from the group consisting of binding to a canine COX-2 molecule and hydrolyzing a canine COX-2 protein substrate; and (d) a protein encoded by an allelic variant of a nucleic acid molecule that encodes any protein of (a), (b), or (c); with a putative inhibitory compound under conditions in which, in the absence of the compound, the protein has canine COX-2 protein activity; and determining if the putative inhibitory compound inhibits the activity.

Another embodiment of the present invention is an assay kit to identify an inhibitor of a canine COX-2 protein of the present invention. This kit comprises an isolated canine COX-2 protein of the present invention, and a means for determining inhibition of an activity of canine COX-2 protein, where the means enables detection of inhibition. Detection of inhibition of canine COX-2 protein identifies a putative inhibitor to be an inhibitor of a canine COX-2 protein. Means for determining inhibition of a canine COX-2 protein include, for example, an assay system that detects binding of a putative inhibitor to a canine COX-2 molecule, and an assay system that detects interference by a putative inhibitor of the ability of canine COX-2 protein to hydrolyze a substrate. Means and methods are described herein and are known to those skilled in the art.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This example describes the isolation, characterization and expression of a COX-2 nucleic acid molecule of the present invention from a canine Con-A stimulated PBMC cDNA library.

A canine COX-2 nucleic acid molecule of about 542 nucleotides was isolated from a canine Con-A stimulated PBMC cDNA library, prepared as described in PCT publication WO 99/61618, in a nested PCR amplification as follows. In a first PCR reaction, sense primer Cox2-1aFOR, having a nucleotide sequence 5' TWY TAY GGN GAR AAY TGY 3', denoted SEQ ID NO:17 was used in combination with reverse primer Cox2-5REV, having a nucleic acid sequence 5'CCY TTN ACR TTR TTR CAD AT 3', denoted SEQ ID NO:18, using the canine Con-A stimulated PBL cDNA library as the template under the following PCR reaction and thermocycling conditions: (1) one cycle of 95° C. for 10 seconds; (2) five cycles of 95° C. for 10 seconds, 55° C. for 40 seconds, and 72° C. for 50 seconds; and (3) twenty-eight cycles of 95° C. for 10 seconds, 52° C. for 20 seconds, and 72° C. for 60 seconds in a reaction containing 0.5 µM of primers, 0.2 mM dNTP's, 2.0 units of Taq polymerase, and 0.5 units of Pfu polymerase, in 1× Taq reaction buffer, referred to hereinafter as "standard PCR reaction conditions". The reaction product from the first PCR reaction was used as the template in a second PCR reaction under the same conditions using sense primer Cox2-1FOR, having a nucleotide sequence 5'CAY TTY AAR GGN GTN TGG AA 3', denoted SEQ ID NO:19 in combination with reverse primer Cox2-3REV, having a nucleotide sequence 5'CCA DAT NGT NOC RTA CAT CAT 3', denoted SEQ ID NO:20. A 542-nucleotide fragment, denoted nCfCX2$_{542}$, having a coding strand designated SEQ ID NO:1 and a complementary strand designated SEQ ID NO:3, was isolated and shown to encode a partial length protein of 180 amino acids, designated SEQ ID NO:2, assuming a first codon spanning from nucleotide 2 through nucleotide 4 of SEQ ID NO:1 and a last codon spanning from nucleotide 539 through nucleotide 541 of SEQ ID NO:1.

Nucleic acid molecule nCfCX2$_{542}$ was $^{32}$P α-dATP labeled and used as a probe in a standard plaque lift hybridization procedure to isolate a clone from the canine Con A stimulated PBMC cDNA library. The following hybridization conditions were used: filters were hybridized with about 1×10$^6$ counts per minute (cpm) per ml of the probe in 5×SSPE, (see Sambrook et al., ibid.), 1% sarcosyl, 0.1% nonfat dry milk and 5×Denhardt's reagent, (see Sambrook et al., ibid.), at 45° C. for about 14 hours. Following hybridization, two washes were performed in 0.5× SSPE, 0.1% sarcosyl at 60° C. for about 10 minutes per wash. Two positive plaques that hybridized strongly to the probe were carried through successive plaque screening until plaque purity was achieved then subjected to in vivo excision. In vivo excision was performed using the Stratagene Ex-Assist™ helper phage system and protocols, to convert a positive plaque to pBluescript™ plasmid DNA. Sequencing was conducted using standard sequencing methods following preparation of DNA with a Bio Rad Quantum Prep Kit, using the manufacturer's instructions.

The longest clone contained a nucleic acid molecule of about 3509 base pairs, referred to herein as nCfCX2$_{3509}$, having a nucleotide sequence denoted herein as SEQ ID NO:4. The complement of SEQ ID NO:4 is represented herein as SEQ ID NO:6. Translation of SEQ ID NO:4 suggests that nucleic acid molecule nCfCX2$_{3509}$ encodes a full-length COX-2 protein of 604 amino acids, referred to herein as PCfCX2$_{604}$, having an amino acid sequence represented by SEQ ID NO:5, assuming the initiation codon spans from nucleotide 53 through nucleotide 55 of SEQ ID NO:4 and the termination codon spans from nucleotide 1865 through nucleotide 1867 of SEQ ID NO:4. The coding region encoding PCICX2$_{604}$, is represented by nucleic acid molecule nCfCX2$_{1812}$, having a coding strand with the nucleic acid sequence represented by SEQ ID NO:7 and a complementary strand with nucleic acid sequence represented by SEQ ID NO:8. The amino acid sequence of PCfCX2$_{604}$, predicts that PCfCX2$_{604}$ has an estimated molecular weight of about 69 kilodaltons (kDa) and an estimated isoelectric point (pI) of about 7.2.

Comparison of amino acid sequence SEQ ID NO:5 with amino acid sequences reported in GenBank indicates that SEQ ID NO:5 showed the most homology, i.e., about 93% identity, with a horse COX-2 protein, GenBank Accession No. AA0791111. Comparison of SEQ ID NO:4 with nucleic acid sequences reported in SenBank indicates that SEQ ID NO:4 showed the most homology, i.e., about 89% identity, with a *Mustela vison* is (mink) prostaglandin synthase-2 mRNA nucleic acid molecule, GenBank Accession number AF047841. Percent identity calculations were performed by pair-wise comparison with the Needleman-Wunsch algorithm, available in the SeqLab Wisconsin Package Version 10.0-UNIX software, using the Pairwise Comparison/Gap function with the nwsgapdna.cmp scoring matrix, the gap creation penalty and the gap extension penalties set at default values, and the gap shift limits set at maximum.

Full-length tagged and untagged COX-2 proteins were produced as follows. A-V5 tagged protein was produced as follows. A PCR reaction was performed using SEQ ID NO:7 (i.e. the COX-2 coding region) as template, using forward primer Cox2BamH1senIselect, having a nucleotide sequence 5' AAG GAT CCG ATA TGC TGG CCC GCG CCC TGG TG 3', having a BamI site shown in bold, designated herein as SEQ ID NO:21, in conjunction with reverse primer Cox2R1asn+tagIselect, having a nucleotide sequence 5' AAG AAT TCC CTA GTT CAG TTG ACC GTT CTT TC 3', having an EcoR1 site shown in bold, designated herein as SEQ ID NO:22, using standard PCR reaction conditions set forth above using the following thermocycling conditions: (1) 95° C. for 60 seconds; and (2) thirty cycles of 94° C. for 10 seconds, 50° C. for 30 seconds, and 69° C. for 90 seconds. This PCR reaction created a PCR product consisting of the COX-2 coding region flanked by BamHI and EcoRI restriction sites on the 5' and 3' ends respectively and a C-terminal V5 tag. An untagged COX-2 protein was produced as follows. A PCR reaction was performed using SEQ ID NO:7 (i.e. the COX-2 coding region) as template, using forward primer Cox2-BamH1senIselect (i.e. SEQ ID NO:21), in conjunction with reverse primer Cox2R1-asnnotag-Iselect, having a nucleotide sequence 5' AAG AAT TCC TAT AGT TCA GTT GAC CGT TCT TTC 3', having an EcoR1 site shown in bold, designated herein as SEQ ID NO:23, using the standard PCR reaction conditions set forth above using the following thermocycling conditions: (1) 95° C. for 60 seconds; and (2) thirty cycles of 94° C. for 10 seconds, 50° C. for 30 seconds, and 69° C. for 90 seconds. This PCR reaction created a PCR product consisting of the COX-2 coding region flanked by BamHI and EcoRI restriction sites on the 5' and 3' ends respectively.

The products from the PCR reactions described above were each digested with BamH1 and EcoRI restriction enzymes and ligated into the vector pIZ/V5-His which had been digested with BamH1 and EcoRI to create V5-tagged and untagged versions of recombinant molecule pIZ/V5-His-nCfCX2$_{1812}$. Plasmid DNA from the V5-tagged and untagged versions was harvested and used to transfect High Five™ (*Tricuplusia ni*) insect cells, available from Invitrogen, using Cell-Fectin™, available from Gibco BRL, per the manufacturers protocols, to form V5-tagged and untagged versions of recombinant cell H5-pIZ/V5-His-nCfCX2$_{1812}$. Cells were selected with zeocin antibiotic to create stable cell lines.

Expression of protein from cell culture supernatants was confirmed by Western blot using an anti-V5 tag antibody which showed expression of an about 70 kDa protein. Enzymatic activity of the expressed protein was confirmed using a Biotrak PGE$_2$ enzymeimmunoassay, available from Amersham Pharmacia, which measures PGE$_2$, the metabolite derived from arachidonic acid due to COX-2 enzyme activity. This assay showed that the recombinantly expressed tagged canine COX-2 in Hi-5 cells was enzymatically active following the addition of exogenous arachidonic acid. Negative controls consisting of Hi-5 cells transfected with and expressing a flea GABA receptor extracellular domain protein showed no COX-2 activity.

EXAMPLE 2

This example describes the isolation and characterization of a COX-1 nucleic acid molecule of the present invention from a lymph node cDNA library.

A canine COX-1 nucleic acid molecule of about 275 nucleotides was independently isolated from a canine lymph node cDNA library, prepared as described in PCT publication WO 99/61618, by PCR amplification as follows. Sense primer Coxlsen, having a nucleotide sequence 5 TTT GCA CAA CAC TTC ACC CAC CAG 3', denoted SEQ ID NO:24 was used in combination with reverse primer Coxlasn, having a nucleic acid sequence 5' AAA CAC CTC CTG GCC CAC AGC CAT 3', denoted SEQ ID NO:25, using the canine Con-A stimulated PBL cDNA library as the template under the standard PCR reaction conditions set forth above using the following thermocycling conditions: (1) one cycle of 94° C. for 60 seconds; (2) five cycles of 94° C. for 20 seconds, 53° C. for 20 seconds, and 72° C. for 20 seconds; and (3) thirty cycles of 94° C. for 20 seconds, 56° C. for 20 seconds, and 72° C. for 30 seconds. A 275-nucleotide fragment, denoted nCfCX1$_{275}$, having a coding strand designated SEQ ID NO:9 and a complementary strand designated SEQ ID NO:11, was isolated and shown to encode a partial length protein of 91 amino acids, designated SEQ ID NO:10, assuming a first codon spanning from nucleotide 1 through nucleotide 3 of SEQ ID NO:9 and a last codon spanning from nucleotide 271 through nucleotide 273 of SEQ ID NO:9.

Nucleic acid molecule nCfCX1$_{275}$ was $^{32}$P α-dATP labeled and used as a probe in a standard plaque lift hybridization procedure to isolate a clone from a canine lymph node cDNA library using hybridization and wash conditions as described in Example 2. A positive plaque that hybridized strongly to the probe was carried through successive plaque screening until plaque purity was achieved then subjected to in vivo excision. In vivo excision was performed using the Stratagene Ex-Assist™ helper phage system and protocols, to convert a positive plaque to pBluescript™ plasmid DNA. Sequencing was conducted using standard sequencing methods following preparation of DNA with a Bio Rad Quantum Prep Kit using the manufacturer's instructions.

The isolated clone contained a nucleic acid molecule of about 2693 base pairs, referred to herein as nCfCX1$_{2693}$, having a nucleotide sequence denoted herein as SEQ ID NO:12. The complement of SEQ ID NO:12 is represented herein as SEQ ID NO:14. Translation of SEQ ID NO:12 suggests that nucleic acid molecule nCfCX1$_{2693}$ encodes a full-length COX-1 protein of 633 amino acids, referred to herein as PCfCX1$_{633}$, having an amino acid sequence represented by SEQ ID NO:13, assuming the initiation codon spans from nucleotide 31 through nucleotide 33 of SEQ ID NO:12 and the termination codon spans from nucleotide 1930 through nucleotide 1932 of SEQ ID NO:12. The coding region encoding PCfCX1$_{633}$, is represented by nucleic acid molecule nCfCX1$_{1899}$, having a coding strand with the nucleic acid sequence represented by SEQ ID NO:15 and a complementary strand with nucleic acid sequence represented by SEQ ID NO:16. The amino acid sequence of PCfCX1$_{633}$, predicts that PCfCX1$_{633}$ has an estimated molecular weight of about 72.5 kilodaltons (kDa) and an estimated isoelectric point (pI) of about 7.5.

Comparison of amino acid sequence SEQ ID NO:13 with amino acid sequences reported in GenBank indicates that SEQ ID NO:13 showed the most homology, i.e., about 92% identity, with a human COX-1 protein, GenBank Accession No. P23219. Comparison of SEQ ID NO:12 with nucleic acid sequences reported in GenBank indicates that SEQ ID NO:12 showed the most homology, i.e., about 87% identity, with a sheep COX-1 nucleic acid molecule, GenBank Accession number M18243.1. Percent identity calculations were performed by pair-wise comparison with the Needleman-Wunsch algorithm, available in the SeqLab Wisconsin Package Version 10.0-UNIX software, using the Pairwise Comparison/Gap function with the nwsgapdna.cmp scoring matrix, the gap creation penalty and the gap extension penalties set at default values, and the gap shift limits set at maximum.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated protein encoded by a nucleic acid sequence that hybridizes with a polynucleotide sequence consisting of SEQ ID NO:3, SEQ ID NO:6 or SEQ ID NO:8, under conditions comprising (i) hybridizing in a solution comprising 1×SSC in the absence of helix destabilizing compounds, at a temperature of about 37° C. and (ii) washing in a solution comprising 1×SSC in the absence of helix destabilizing compounds, at a temperature of about 81° C., wherein said isolated protein has cyclooxygenase activity.

2. The isolated protein of claim 1, wherein said nucleic acid sequence is at least 95% identical to SEQ ID NO:1, SEQ ID NO:4 or SEQ ID NO:7.

3. The isolated protein of claim 1, wherein said nucleic acid sequence is at least 98% identical to SEQ ID NO:1, SEQ ID NO:4 or SEQ ID NO:7.

4. The isolated protein of claim 1, wherein said nucleic acid sequence is identical to SEQ ID NO:1, SEQ ID NO:4 or SEQ ID NO:7.

5. An isolated protein selected from the group consisting of:
   (a) an isolated protein comprising an amino acid sequence at least 95% identical to SEQ ID NO:2 or SEQ ID NO:5; and
   (b) an isolated protein comprising at least 115 contiguous amino acids from SEQ ID NO:5;

wherein said isolated protein has cyclooxygenase activity.

6. The isolated protein of claim 5, wherein said protein comprises at least 300 contiguous amino acids from SEQ ID NO:5.

7. The isolated protein of claim 5, wherein said amino acid sequence is at least 98% identical to SEQ ID NO:2 or SEQ ID NO:5.

8. The isolated protein of claim 5, wherein said amino acid sequence is identical to SEQ ID NO:2 or SEQ ID NO:5.

9. A method to detect an inhibitor of cyclooxygenase activity, said method comprising:
   (a) contacting an isolated protein with a putative inhibitory compound, wherein said isolated protein is encoded by a nucleic acid sequence that hybridizes with a polynucleotide sequence consisting of SEQ ID NO:3, SEQ ID NO:6 or SEQ ID NO:8, under conditions comprising (i) hybridizing in a solution comprising 1×SSC in the absence of helix destabilizing compounds, at a temperature of about 37° C. and (ii) washing in a solution comprising 1×SSC in the absence of helix destabilizing compounds, at a temperature of about 81° C., wherein said isolated protein has cyclooxygenase activity; and
   (b) determining if said putative inhibitory compound inhibits said cyclooxygenase activity.

10. The method of claim 9, wherein said isolated protein is selected from the group consisting of:

(a) an isolated protein comprising an amino acid sequence at least 95% identical to SEQ ID NO:2 or SEQ ID NO:5; and
(b) an isolated protein comprising at least 115 contiguous amino acids from SEQ ID NO:5.

11. The method of claim 9, wherein said isolated protein is selected from the group consisting of:
(a) an isolated protein comprising an amino acid sequence at least 98% identical to SEQ ID NO:2 or SEQ ID NO:5; and
(b) an isolated protein comprising at least 300 contiguous amino acids from SEQ ID NO:5.

12. The method of claim 9, wherein said isolated protein comprises SEQ ID NO:2 or SEQ ID NO:5.

13. A kit for performing the method of claim 10, said kit comprising:
(a) an isolated protein having cyclooxygenase activity, wherein said protein is encoded by a nucleic acid sequence that hybridizes with a polynucleotide sequence consisting of SEQ ID NO:3, SEQ ID NO:6 or SEQ ID NO:8, under conditions comprising (i) hybridizing in a solution comprising 1×SSC in the absence of helix destabilizing compounds, at a temperature of about 37° C. and (ii) washing in a solution comprising 1×SSC in the absence of helix destabilizing compounds, at a temperature of about 8120 C., and
(b) a means for detecting the inhibition of said cyclooxygenase activity.

14. The kit of claim 13, wherein said isolated protein having cyclooxygenase activity is selected from the group consisting of:
(a) an isolated protein comprising an amino acid sequence at least 95% identical to SEQ ID NO:2 or SEQ ID NO:5; and
(b) an isolated protein comprising at least 115 contiguous amino acids from SEQ ID NO:5.

15. The kit of claim 13, wherein said isolated protein having cyclooxygenase activity is selected from the group consisting of:
(a) an isolated protein comprising an amino acid sequence at least 98% identical to SEQ ID NO:2 or SEQ ID NO:5; and
(b) an isolated protein comprising at least 300 contiguous amino acids from SEQ ID NO:5.

* * * * *